US008715966B2

(12) United States Patent
Xiaohai et al.

(10) Patent No.: US 8,715,966 B2
(45) Date of Patent: May 6, 2014

(54) PREPARATION OF TEMPLATES FOR NUCLEIC ACID SEQUENCING

(75) Inventors: Liu Xiaohai, Nr Saffron Walden (GB); John Milton, Nr Saffron Walden (GB); Geoffrey Paul Smith, Nr Saffron Walden (GB); Colin Lloyd Barnes, Trumpington (GB); Isabelle Marie Julia Rasolonjatovo, Nr Saffron Walden (GB); Roberto Rigatti, Nr Saffron Walden (GB); Xiaolin Wu, Nr Saffron Walden (GB); Tobias William Barr Ost, Nr Saffron Walden (GB); Graham John Worsley, Nr Saffron Walden (GB); David James Earnshaw, Nr Saffron Walden (GB); Gerardo Turcatti, Geneva (CH); Anthony Romieu, Rouen (FR)

(73) Assignee: Illumina Cambridge Limited, Nr Saffron Walden (GB)

( * ) Notice: Subject to any disclaimer, the term of this patent is extended or adjusted under 35 U.S.C. 154(b) by 0 days.

(21) Appl. No.: 13/450,920

(22) Filed: Apr. 19, 2012

(65) Prior Publication Data
US 2012/0208194 A1 Aug. 16, 2012

Related U.S. Application Data

(63) Continuation of application No. 11/989,169, filed as application No. PCT/GB2006/002687 on Jul. 2, 2006, now abandoned.

(30) Foreign Application Priority Data

Jul. 20, 2005 (GB) .................................. 0514936.4

(51) Int. Cl.
C12Q 1/68 (2006.01)
C12P 19/34 (2006.01)
C40B 40/06 (2006.01)
(52) U.S. Cl.
USPC .............................. 435/91.2; 435/6.1; 506/16
(58) Field of Classification Search
None
See application file for complete search history.

(56) References Cited

U.S. PATENT DOCUMENTS

| 6,300,070 B1 | 10/2001 | Boles et al. |
| 6,372,813 B1 | 4/2002 | Johnson et al. |
| 6,949,633 B1 * | 9/2005 | Monforte et al. ............ 536/22.1 |
| 2002/0127575 A1 | 9/2002 | Hoke et al. |
| 2008/0280773 A1 * | 11/2008 | Fedurco et al. .................. 506/9 |

FOREIGN PATENT DOCUMENTS

| WO | 98/28440 | 7/1998 |
| WO | 98/44151 | 10/1998 |
| WO | WO-98/44151 | 10/1998 |
| WO | WO-00/18957 | 4/2000 |
| WO | 00/31148 | 6/2000 |
| WO | WO-00/53617 | 9/2000 |
| WO | WO-00/58329 | 10/2000 |
| WO | 00/75374 | 12/2000 |
| WO | 01/62982 | 8/2001 |
| WO | WO-01/62982 | 8/2001 |
| WO | WO-03/014392 | 2/2003 |
| WO | WO2004/011665 | 2/2004 |
| WO | WO-2004/016767 | 2/2004 |
| WO | 2005/040425 | 5/2005 |
| WO | WO-2005/065814 | 7/2005 |
| WO | WO 2005065814 A1 * | 7/2005 |
| WO | WO 2006064199 A1 * | 6/2006 |

OTHER PUBLICATIONS

Mitra, et al., "Fluorescent in situ sequencing on polymerase colonies", Analytical Biochemistry, Academic Press, San Diego US vol. 320 No. 1, 2002, 55-65.
Notice of Opposition, , "European Application No. 10011728.2", mailed Sep. 9, 2013.
Fu, et al., "Sequencing Double-stranded DNA by Strand Displacement", Nucleic Acids Research vol. 25 No. 3, 1997, 677-679.
Gulrez, K.H. S., "Hydrogels: Methods of Preparation, Characterisation and Applications", Progress in Molecular and Environmental Bioengineering—From Analysis and Modeling to Technology Applications; www.intechopen.com, 117-150, 2011.
Rehman, Farah N. et al., "Immobilization of acrylamide-modified oligonucleotides by co-polymerization", Nucleic Acids Research, 27 (2), 1999, 649-655.
Opposition against EP 1 910 559 B1, filed on Mar. 12, 2013.

* cited by examiner

*Primary Examiner* — Christina Bradley
*Assistant Examiner* — Lianko Garyu
(74) *Attorney, Agent, or Firm* — Brent C. Moore; Illumina, Inc.

(57) ABSTRACT

The invention relates to methods of generating templates for a nucleic acid sequencing reaction which comprise: providing at least one double-stranded nucleic acid molecule, wherein both strands of the double-stranded nucleic acid molecule are attached to a solid support at the 5' end, cleaving one or both strands of the double-stranded nucleic acid molecule, and subjecting the cleaved strand(s) to denaturing conditions to remove the portion of the cleaved strand(s) not attached to the solid support, thereby generating a partially or substantially single-stranded template for a nucleic acid sequencing reaction.

11 Claims, 8 Drawing Sheets

(a) (b)

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
tcggtggtcg ccgtatcatt                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
gtagactgca tgacctgtag                    20

<210> SEQ ID NO 3
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 3
tttttttttt aatgatacgg cgaccaccga                                  30

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
aatgatacgg cgaccaccga                                             20

<210> SEQ ID NO 5
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 5
tttttttttt caagcagaag acggcatacg a                                31

<210> SEQ ID NO 6
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 6
ctggcacgac aggtttcccg actggaaagc gggcagtg                         38

<210> SEQ ID NO 7
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 7
acactctttc cctacacgac gctcttccga tc                               32

<210> SEQ ID NO 8
<211> LENGTH: 364
<212> TYPE: DNA
<213> ORGANISM: Artificial Sequence
<220> FEATURE:
<223> OTHER INFORMATION: Synthetic Sequence

<400> SEQUENCE: 8
caagcagaag acggcatacg agcatagaga ccgagagaag atcggaagag cgtcgtgtag    60
ggaaagagtg tgagatcttt tatcatctcc ataaacaaa acccgccgta gcgagttcag   120
ataaaataaa tccccgcgag tgcgaggatt gttatgtaat attgggttta atcatctata   180
tgttttgtac agagagggca agtatcgttt ccaccgtact cgtgataata atttgcacg    240 gtatcagtca tttctcgcac attgcagaat ggggatttgt cttcattaga cttataaacc   300

```
ttcatggaat atttgtatgc cgactctata tctataactt catctcggtg gtcgccgtat    360
catt                                                                 364

<210> SEQ ID NO 9
<211> LENGTH: 89
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (65)..(65)
<223> OTHER INFORMATION: n is a, c, g, or t

<400> SEQUENCE: 9
aatgatacgg cgaccaccga gatctggcac gacaggtttc ccgactggaa agcgggcagt    60
ggatnatctc gtatgccgtc ttctgcttg                                      89

<210> SEQ ID NO 10
<211> LENGTH: 89
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (65)..(65)
<223> OTHER INFORMATION: n is a, c, g, or t

<400> SEQUENCE: 10
ttactatgcc gctggtggct ctagaccgtg ctgtccaaag ggctgacctt tcgcccgtca    60
cctantagag catacggcag aagacgaac                                      89

<210> SEQ ID NO 11
<211> LENGTH: 364
<212> TYPE: DNA
<213> ORGANISM: Artificial Sequence
<220> FEATURE:
<223> OTHER INFORMATION: Synthetic Sequence

<400> SEQUENCE: 11
gttcgtcttc tgccgtatgc tcgtatctct ggctctcttc tagccttctc gcagcacatc    60
cctttctcac actctagaaa atagtagagg tattttgttt tgggcggcat cgctcaagtc    120
tattttattt aggggcgctc acgctcctaa caatacatta taccccaaat tagtagatat    180
acaaaacatg tctctcccgt tcatagcaaa ggtggcatga gcactattat taaaacgtgc    240
catagtcagt aaagagcgtg taacgtctta cccctaaaca gaagtaatct gaatatttgg    300
aagtacctta taaacatacg gctgagatat agatatggaa gtagagccac cagcggcata    360
gtaa                                                                 364
```

PREPARATION OF TEMPLATES FOR NUCLEIC ACID SEQUENCING

CROSS REFERENCE TO RELATED APPLICATIONS

The present application is a continuation of U.S. Ser. No. 11/989,169, filed Dec. 22, 2008 now abandoned, which is a National Stage Application of PCT Application No. PCT/GB2006/002687, filed Jul. 20, 2006, which in turn, claims priority from Great Britain Application Serial No. GB 0514936.4, filed Jul. 20, 2005. The entire disclosures of these applications are incorporated herein by reference in their entireties.

FIELD OF THE INVENTION

The invention relates to the preparation of templates for nucleic acid sequencing reactions and to methods of sequencing such templates. In particular, the invention relates to the preparation of template nucleic acid molecules ready for sequencing by cleavage of one or both strands of a double-stranded nucleic acid immobilised on a solid support.

BACKGROUND TO THE INVENTION

Nucleic acid sequencing methods have been known in the art for many years. One of the best-known methods is the Sanger "dideoxy" method which relies upon the use of dideoxyribonucleoside triphosphates as chain terminators. The Sanger method has been adapted for use in automated sequencing with the use of chain terminators incorporating fluorescent labels.

There are also known in the art methods of nucleic acid sequencing which are based on successive cycles of incorporation of fluorescently labelled nucleic acid analogues. In such "sequencing by synthesis" or "cycle sequencing" methods the identity of the added base is determined after each nucleotide addition by detecting the fluorescent label.

In particular, U.S. Pat. No. 5,302,509 describes a method for sequencing a polynucleotide template which involves performing multiple extension reactions using a DNA polymerase or DNA ligase to successively incorporate labelled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

In order to maximise the throughput of nucleic acid sequencing reactions it is advantageous to be able to sequence multiple template molecules in parallel. Parallel processing of multiple templates can be achieved with the use of nucleic acid array technology. These arrays typically consist of a high-density matrix of polynucleotides immobilised onto a solid support material.

Various methods for fabrication of arrays of immobilised nucleic assays have been described in the art. Of particular interest, WO 98/44151 and WO 00/18957 both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. Arrays of this type are referred to herein as "clustered arrays". The nucleic acid molecules present in DNA colonies on the clustered arrays prepared according to these methods can provide templates for sequencing reactions, for example as described in WO 98/44152.

The products of solid-phase amplification reactions such as those described in WO 98/44151 and WO 00/18957 are so-called "bridged" structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard hybridisation conditions.

In order to provide more suitable templates for nucleic acid sequencing it is preferred to remove substantially all or at least a portion of one of the immobilised strands in the "bridged" structure in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearisation".

It is known in the art that bridged template structures may be linearised by cleavage of one or both strands with a restriction endonuclease. A disadvantage of the use of restriction enzymes for linearisation is that it requires the presence of a specific recognition sequence for the enzyme at a suitable location in the bridged template structure. There is a risk that the same recognition sequence may appear elsewhere in the bridged structure, meaning that the enzyme may cut at one or more further sites, in addition to the intended cleavage site for linearisation. This may be a particular problem where the bridged structures to be linearised are derived by solid-phase amplification of templates of partially unknown sequence, since it cannot be predicted in advance whether a particular enzyme will cut within the region of unknown sequence.

Therefore, in one general aspect the invention provides methods of template linearisation which do not require cleavage with restriction endonucleases, or with nicking endonucleases.

In another general aspect the invention relates to methods of template linearisation which are compatible with a particular type of solid supported microarray. More specifically, the invention provides linearisation methods which are compatible with arrays formed on solid supported polyacrylamide hydrogels.

In preparing hydrogel-based solid-supported molecular arrays, a hydrogel is formed and molecules displayed from it. These two features—formation of the hydrogel and construction of the array—may be effected sequentially or simultaneously. Where the hydrogel is formed prior to formation of the array, it is typically produced by allowing a mixture of co-monomers to polymerise. Generally, the mixture of co-monomers contain acrylamide and one or more co-monomers, the latter of which permit, in part, subsequent immobilisation of molecules of interest so as to form the molecular array.

The co-monomers used to create the hydrogel typically contain a functionality that serves to participate in crosslinking of the hydrogel and/or immobilise the hydrogel to the solid support and facilitate association with the target molecules of interest.

The present inventors have shown that clustered arrays may be formed on such solid-supported hydrogels by solid phase nucleic acid amplification using forward and reverse amplification primers attached to the hydrogel at their 5' ends, leading to the production of clustered arrays of amplification products having a "bridged" structure. In order to maximise the efficiency of sequencing reactions using templates derived from such bridged products there is a need for linearisation methods which are compatible with the hydrogel surface and with subsequent nucleic acid sequencing reactions.

SUMMARY OF THE INVENTION

In a first aspect the invention provides a method of generating a template for a nucleic acid sequencing reaction comprising,
(i) providing a solid supported polyacrylamide hydrogel having attached thereto one or more double-stranded nucleic acid molecules, wherein both strands of the double-stranded nucleic acid molecule are attached to the polyacrylamide hydrogel at the 5' end,
(ii) cleaving one or both strands of the double-stranded nucleic acid molecule, and
(iii) subjecting the cleaved strand(s) to denaturing conditions to remove the portion of the cleaved strand(s) not attached to the polyacrylamide hydrogel, thereby generating a partially or substantially single-stranded template for a nucleic acid sequencing reaction.

In a preferred embodiment of this aspect of the invention step (ii) does not comprise cleavage with a restriction endonuclease or a nicking endonuclease.

In a second aspect the invention provides method of generating a template for a nucleic acid sequencing reaction comprising,
(i) providing at least one double-stranded nucleic acid molecule, wherein both strands of the double-stranded nucleic acid molecule are attached to a solid support at the 5' end,
(ii) cleaving one or both strands of the double-stranded nucleic acid molecule, and
(iii) subjecting the cleaved strand(s) to denaturing conditions to remove the portion of the cleaved strand(s) not attached to the solid support, thereby generating a partially or substantially single-stranded template for a nucleic acid sequencing reaction,
characterised in that step (ii) does not comprise cleavage with a restriction endonuclease or a nicking endonuclease.

In one embodiment of both the first and second aspects of the invention the double-stranded stranded nucleic acid molecule may be cleaved at a pre-determined cleavage site. By "pre-determined" cleavage site is meant a site whose location is determined in advance of the cleavage reaction, as opposed to cleavage at a random site the location of which is not known in advance.

In one embodiment of both the first and second aspects of the invention cleavage may occur at a cleavage site in one or both strands of the double-stranded nucleic acid molecule which comprises one or more or any combination of non-natural nucleotides, ribonucleotides or a non-nucleotide chemical modifications. The position of this cleavage site is preferably pre-determined.

In one embodiment of both the first and second aspects of the invention the double-stranded nucleic acid molecule may be cleaved in one or both strands via a non-enzymatic chemical cleavage reaction. In a specific non-limiting embodiment one strand of the double-stranded nucleic acid molecule may comprise a diol linker and this strand may be cleaved by treatment with periodate.

In a further embodiment of both the first and second aspects of the invention one strand of the double-stranded nucleic acid molecule may be treated to generate an abasic site and then cleaved at the abasic site. In a non-limiting specific embodiment, wherein one strand of the double-stranded nucleic acid molecule includes a uracil base, the abasic site may be generated by treatment with uracil DNA glycosylase and then cleaved with endonuclease, heat treatment or alkali treatment.

In a further embodiment of both the first and second aspects of the invention one strand of the double-stranded nucleic acid may comprise one or more ribonucleotides and step (ii) may comprise cleaving this strand adjacent to a ribonucleotide using an RNAse or a non-enzymatic chemical cleavage agent. Suitable non-enzymatic chemical cleavage agents include metal ions, and in particular rare earth metal ions, e.g. $La^{3+}$ or $Lu^{3+}$.

In a further embodiment of both the first and second aspects of the invention one strand of the double-stranded nucleic acid may comprise one or more methylated nucleotides and step (ii) may comprise cleaving this strand using an enzyme specific for a recognition sequence including said methylated nucleotide(s).

In a further embodiment of both the first and second aspects of the invention step (ii) may comprise cleaving one or both strands of the double-stranded nucleic acid in a photochemical reaction.

In a further embodiment of the first and second aspects of the invention one strand of the double-stranded nucleic acid molecule may have a peptide covalently linked at the 5' end and step (ii) may comprise cleaving the peptide.

In a third aspect the invention also provides methods of sequencing nucleic acid templates generated according to the methods of the first and second aspects of the invention.

The present invention will now be further described. In the following passages different features of the various aspects of the invention are defined in more detail. Each feature so defined in connection with one aspect of the invention may be combined with features described in connection with any other aspect of the invention unless clearly indicated to the contrary. In particular, any feature indicated as being preferred or advantageous may be combined with any other feature or features indicated as being preferred or advantageous.

BRIEF DESCRIPTION OF THE DRAWINGS

FIG. 1(b) schematically illustrates the "bridged" amplification products resulting from solid phase amplification. For simplicity only a small number of bridged products are shown. The amplification products are then "linearised" by cleavage at the cleavage sites derived from the amplification primers (FIG. 1(c)). The products of the cleavage reaction may then be subjected to denaturing conditions, resulting in removal of the portions of the cleaved strands which are no longer covalently attached to the solid support (FIG. 1(d)). The remaining single stranded products may then be hybridised to a sequencing primer (FIG. 1(e)).

FIG. 3(a) shows the sequence of a representative double-stranded nucleic acid molecule (top strand SEQ ID NO:9; bottom strand SEQ ID NO:10) which includes sequences derived from the amplification primers P5 and P7 utilised in the accompanying examples, a restriction site for cleavage by the enzyme BglII and a site for binding of a sequencing primer. "Genomic" represents a sequence derived from a genomic DNA fragment. The genomic fragment will typically be from 400-700 b in length, although the invention is not limited to sequences of this length, and may be of known, partially known or unknown sequence. FIG. 3(b) schematically illustrates linearisation of a single bridged double-stranded nucleic acid product having the sequence shown in FIG. 3(a). The two complementary strands forming the bridged product are covalently attached to a solid support at their 5' ends. The bridged product is first cleaved with BglII and then denatured to remove substantially all of one strand. The single strand remaining on the solid support may then be hybridised to a sequencing primer.

DETAILED DESCRIPTION OF THE INVENTION

Figure 1:
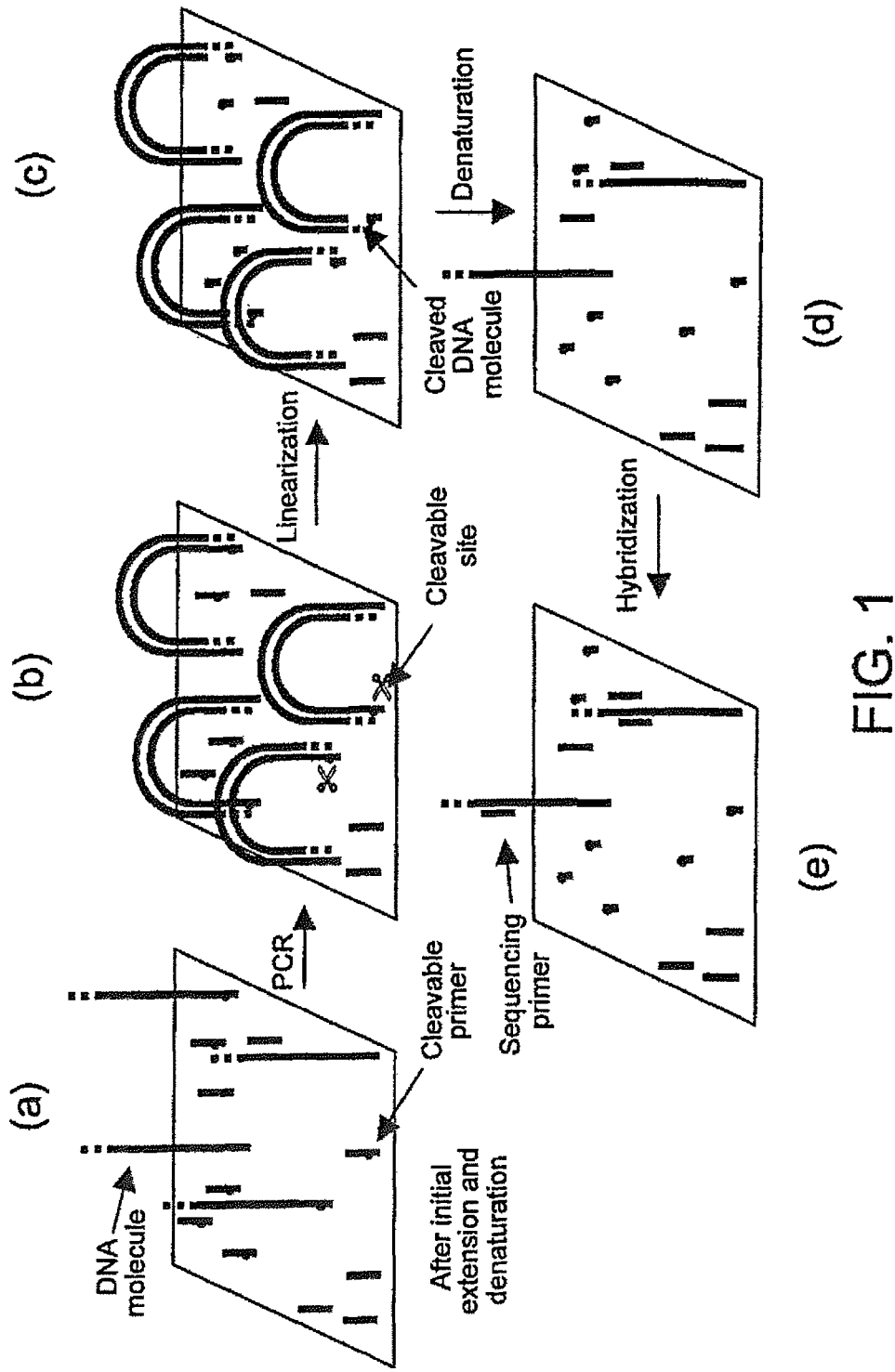
FIG. 1. is a schematic illustration of cluster formation by solid-phase PCR and subsequent linearisation and annealing of a sequencing primer. The starting material in step (a) is a solid support grafted with a mixture of amplification primers, one of which comprises a cleavage site. The primers are covalently attached to the solid support at the 5' end. A substrate molecule to be amplified is also applied to the solid support, either by hybridisation to one of the immobilised primers or by direct covalent attachment to the support at the 5' end.
Figure 2:
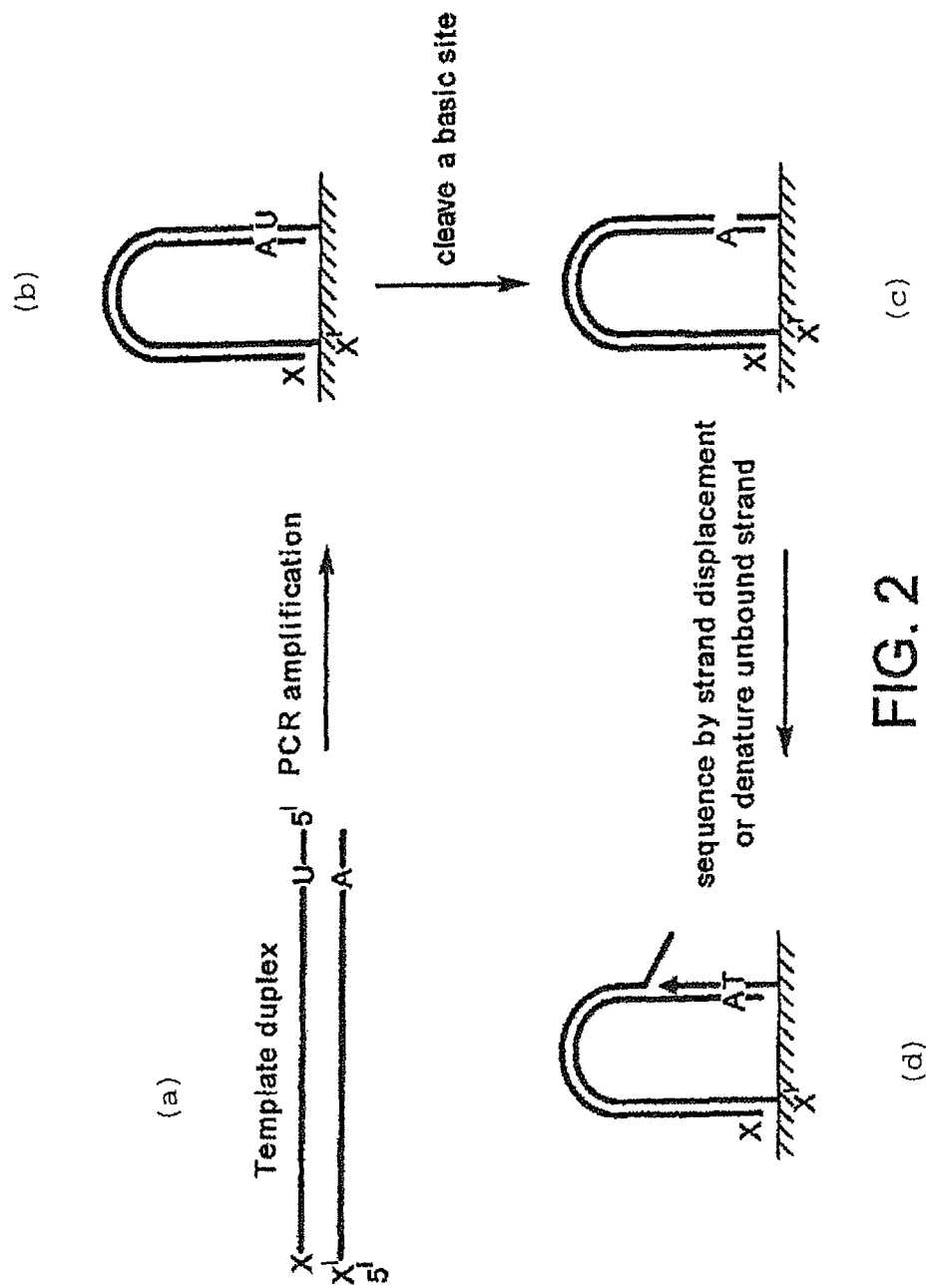
FIG. 2. is a schematic illustration of linearisation by cleavage at an abasic site generated by treatment of a U-containing polynucleotide with uracil DNA glycosylase. Bridged amplification products are generated by amplification of the template structure schematically illustrated in FIG. 2(a) with primers immobilised on a solid support. One of the amplification primers contains a deoxyuridine nucleotide represented as U. A single bridged product is illustrated in FIG. 2(b) for simplicity. An abasic site is generated in one strand by treatment with uracil DNA glycosylase. This strand may then be cleaved by hydrolysis of the abasic site to generate the "nicked" structure illustrated in FIG. 2(c). Hydrolysis of the abasic site generates a free 3' hydroxyl group which can serve as an initiation point for a sequencing reaction. Sequencing may be carried out using a strand displacing polymerase (as shown in FIG. 2(d), or the portion of the cleaved strand not attached to the solid support may be removed by denaturation prior to sequencing. In the latter case the sequencing reaction could be initiated by hybridisation of a sequencing primer as an alternative to priming from the cleaved strand itself.
Figure 3:
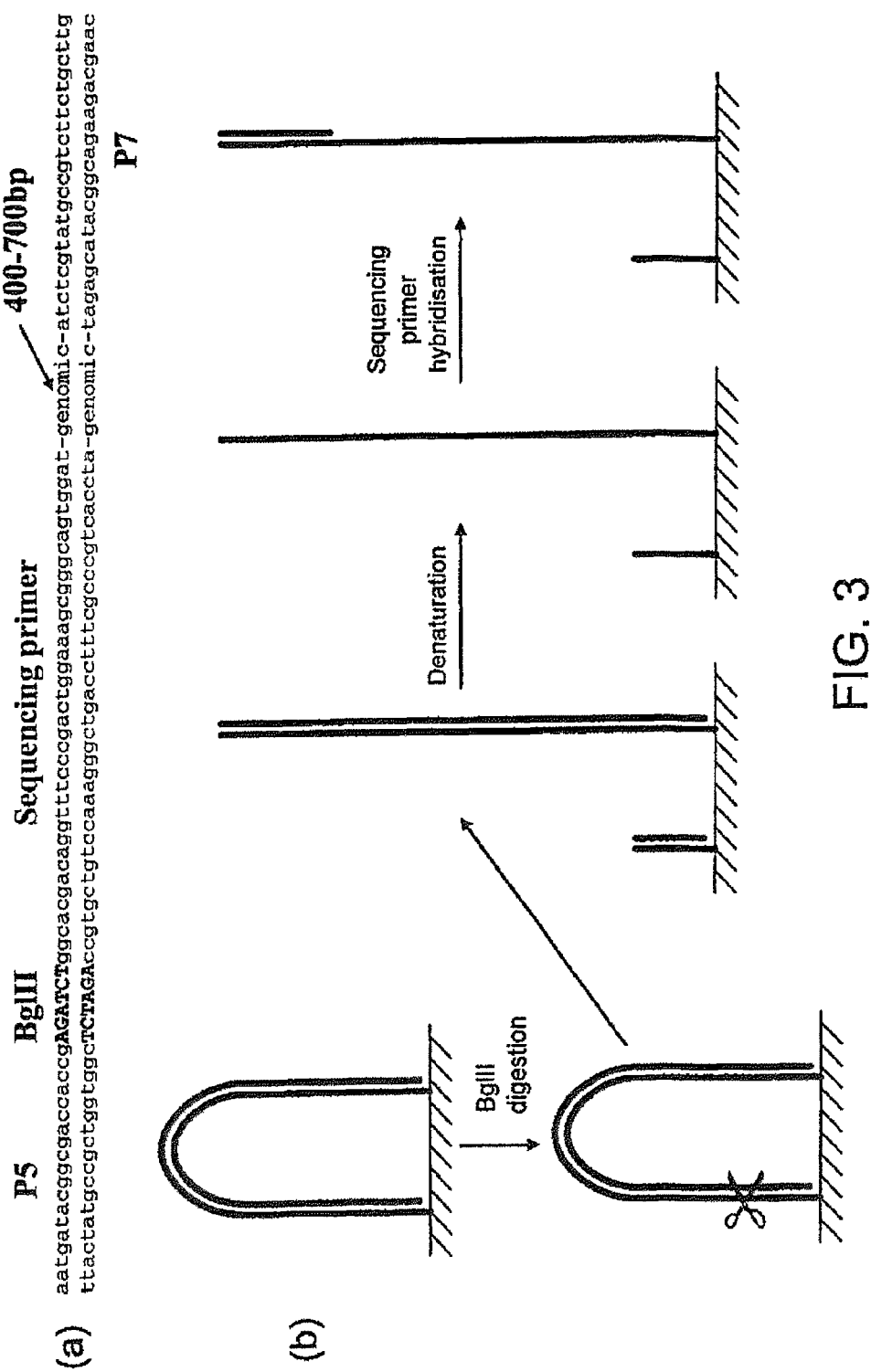
FIG. 3. illustrates linearisation by cleavage with a restriction enzyme.

In its various aspects the invention generally relates to methods of forming templates for nucleic acid sequencing starting from double-stranded nucleic acid molecules immobilised on a solid support, and to methods of sequencing such templates.

The double-stranded nucleic acid molecules which provide the starting point for sequencing template formation according to the first and second aspects of the invention are characterised in that they are formed from annealed complementary nucleic acid strands that are attached to the solid support at their 5' ends, preferably via covalent attachment. When the complementary strands of the double-stranded nucleic acid molecule are annealed, such as will generally be the case when the molecules are maintained under non-denaturing conditions, such molecules may be referred to herein as "bridged" structures.

The methods of template formation provided by the invention involve cleavage of one or both strands of the double-stranded molecule. Following the cleavage step the cleaved products may be subjected to denaturing conditions so as to remove the portion(s) of the cleaved strand(s) which are not attached to the solid support, i.e. the portion located downstream of the site of cleavage when a given strand is viewed 5' to 3'.

The resulting template molecule will be at least partially single-stranded and may be substantially single-stranded. The length of the single-stranded portion will depend on the position of the cleavage site relative to the 5' ends of the complementary strands and whether the cleavage step cuts one or both strands. It will be appreciated that the location of the cleavage site determines how much of each strand remains attached to the solid support after cleavage and denaturation.

The double-stranded nucleic acid molecule from which the sequencing template is to be derived comprises two annealed (complementary) polynucleotide strands which are both attached to a solid support at or near the 5' end. Linkage to the solid support will preferably be via covalent attachment. It will be appreciated that the annealed strands need not necessarily be fully complementary along their entire length.

When referring to attachment of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing.

Certain embodiments of the invention make use of solid supports comprised of an inert substrate or matrix (e.g. glass slides, polymer beads etc) which is been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

In all aspects of the invention, covalent attachment can be achieved through a sulphur-containing nucleophile, such as phosphorothioate, present at the 5' end of a polynucleotide strand. In the case of arrays based on solid-supported polyacrylamide hydrogels, this nucleophile will bind to a "C" group present in the hydrogel.

The "double-stranded" nucleic acid to be cleaved may in fact be partially single-stranded at the 5' end(s) of one or both strands. As will be discussed in further detail hereinbelow, the double-stranded nucleic acid will typically be formed from two complementary polynucleotide strands comprised of deoxyribonucleotides joined by phosphodiester bonds, but may additionally include one or more ribonucleotides and/or non-nucleotide chemical moieties and/or non-naturally occurring nucleotides and/or non-naturally occurring backbone linkages. In particular, the double-stranded nucleic acid may include non-nucleotide chemical moieties, e.g. linkers or spacers, at the 5' end of one or both strands. By way of non-limiting example, the double-stranded nucleic acid may include methylated nucleotides, uracil bases, phosphorothioate groups, also peptide conjugates etc. Such non-DNA or non-natural modifications may be included in order to permit cleavage, or to confer some other desirable property, for example to enable covalent attachment to a solid support, or to act as spacers to position the site of cleavage an optimal distance from the solid support.

The site for cleavage of a strand of the double-stranded nucleic acid may, depending on the nature of the cleavage reaction, be positioned in a region of the molecule that is single-stranded when the complementary strands are annealed. As outlined above, the double-stranded nucleic acid may in fact be partially single-stranded at one or both 5' ends, e.g. proximal to the site of linkage to the solid support. It is within the scope of the invention for a cleavage site to be positioned within such a single-stranded region. In other embodiments the cleavage site may be present in a non-nucleotide chemical moiety covalently attached to the 5' end of one strand of the double-stranded nucleic acid, for example a linker moiety.

The double-stranded nucleic acid will typically comprise a "target" region that it is desired to fully or partially sequence. The nature of the target region is not limiting to the invention. It may be of previously known or unknown sequence and may be derived, for example, from a genomic DNA fragment, a cDNA, etc. The double-stranded nucleic acid molecule may also include non-target sequences, for example at the 5' and 3' ends of both strands, flanking the target region. If the double-stranded nucleic acid is formed by solid-phase nucleic acid amplification, these non-target sequences may be derived from the primers used for the amplification reaction. Sites for cleavage of one or both strands of the double-stranded nucleic acid may be positioned in the non-target sequences.

The double-stranded nucleic acid may form part of a cluster or colony comprised of many such double-stranded nucleic acid molecules, and the cluster or colony may itself form part of an array of such clusters or colonies, referred to herein as a "clustered array". On such an array each double-stranded nucleic acid molecule within each colony will comprise the same target region, whereas different colonies may be formed of double-stranded nucleic acid molecules comprising different target regions. In a preferred embodiment at least 90%, more preferably at least 95% of the colonies on a given clustered array will be formed from double-stranded nucleic acid molecules comprising different target regions, although within each individual colony on the array all double-stranded nucleic acid molecules will comprise the same target region.

On such a clustered array it is preferred that all double-stranded nucleic acid molecules within all of the colonies on the array comprise the same type of cleavage site. This is preferred even when different colonies on the array are formed of double-stranded nucleic acid molecules comprising different target regions, since it enables all the double-stranded molecules on the array to be cleaved simultaneously under identical cleavage reaction conditions.

Cleavage Methods

Various cleavage methods may be used in accordance in accordance with the first and second aspects of the invention to cleave one or both strands of the double-stranded nucleic acid molecule. Preferred but non-limited embodiments of suitable cleavage methods are discussed in further detail below. Methods i) to vii) are common to the first and second aspects of the invention.

i) Chemical Cleavage

The term "chemical cleavage" encompasses any method which utilises a non-nucleic acid and non-enzymatic chemical reagent in order to promote/achieve cleavage of one or both strands of the double-stranded nucleic acid molecule. If required, one or both strands of the double-stranded nucleic acid molecule may include one or more non-nucleotide chemical moieties and/or non-natural nucleotides and/or non-natural backbone linkages in order to permit a chemical cleavage reaction at a pre-determined cleavage site.

In a preferred but non-limiting embodiment one strand of the double-stranded nucleic acid molecule may include a diol linkage which permits cleavage by treatment with periodate (e.g. sodium periodate). The diol linkage may be positioned at a pre-determined cleavage site, the precise location of which may be selected by the user. It will be appreciated that more than one diol could be included at the cleavage site.

Diol linker units based on phosphoamidite chemistry suitable for incorporation into polynucleotide chains are commercially available from Fidelity systems Inc. (Gaithersburg, Md., USA). One or more diol units may be incorporated into a polynucleotide using standard methods for automated chemical DNA synthesis.

In order to position the diol linker at an optimum distance from the solid support one or more spacer molecules may be included between the diol linker and the site of attachment to the solid support. The spacer molecule may be a non-nucleotide chemical moiety. Suitable spacer units based on phosphoamidite chemistry for use in conjunction with diol linkers are also supplied by Fidelity Systems Inc. One suitable spacer for use with diol linkers is the spacer denoted arm 26, identified in the accompanying examples. arm 26 may be modified to include a phosphorothioate group at the 5' end in order to facilitate attachment of the 5' end of the polynucleotide strand to a solid support. The phosphorothioate group can easily be attached during chemical synthesis of a "polynucleotide" chain including the spacer and diol units.

Other spacer molecules could be used as an alternative to arm 26. For example, a stretch of non-target "spacer" nucleotides may be included. Typically from 1 to 20, more preferably from 1 to 15 or from 1 to 10, and more particularly 2, 3, 4, 5, 6, 7, 8, 9 or 10 spacer nucleotides may be included. Most preferably 10 spacer nucleotides will be positioned between the point of attachment of the polynucleotide strand to a solid support (typically the extreme 5' end) and the diol linker. It is preferred to use polyT spacers, although other nucleotides and combinations thereof can be used. In one preferred embodiment the strand to be cleaved may include 10T spacer nucleotides upstream of the diol linker.

The diol linker is cleaved by treatment with a "cleaving agent", which can be any substance which promotes cleavage of the diol. The preferred cleaving agent is periodate, preferably aqueous sodium periodate ($NaIO_4$). Following treatment with the cleaving agent (e.g. periodate) to cleave the diol, the cleaved product may be treated with a "capping agent" in order to neutralize reactive species generated in the cleavage reaction. Suitable capping agents for this purpose include amines, such as ethanolamine. Advantageously, the capping agent (e.g. ethanolamine) may be included in a mixture with the cleaving agent (e.g. periodate) so that reactive species are capped as soon as they are formed.

The combination of a diol linkage and cleaving agent (e.g. periodate) to achieve cleavage of one strand of a double-stranded nucleic acid molecule is preferred for linearisation of nucleic acid molecules on solid supported polyacrylamide hydrogels because treatment with periodate is compatible with nucleic acid integrity and with the chemistry of the hydrogel surface. However, the invention is not intended to be limited to the use of diol linkages/periodate as a method of linearisation on polyacrylamide hydrogel surfaces but also extends to use of this cleavage method for linearisation of nucleic acids immobilised on other surfaces, including supports coated with functionalised silanes (etc).

ii) Cleavage Of Abasic Sites in a Double-Stranded Molecule

An "abasic site" is defined as a nucleoside position in a polynucleotide chain from which the base component has been removed. Abasic sites can occur naturally in DNA under physiological conditions by hydrolysis of nucleoside residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

In a preferred but non-limiting embodiment an abasic site may be created at a pre-determined position on one strand of a double-stranded polynucleotide and then cleaved by first incorporating deoxyuridine (U) at a pre-determined cleavage site in the double-stranded nucleic acid molecule.

This can be achieved, for example, by including U in one of the primers used for preparation of the double-stranded nucleic acid molecule by solid-phase PCR amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g. EndoIV endonuclease, AP lyase, FPG glycosylase/AP lyase, EndoVIII glycosylase/AP lyase), heat or alkali.

Abasic sites may also be generated at non-natural/modified deoxyribonucleotides other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase). If the double-stranded nucleic acid molecule is formed by solid-phase PCR amplification using an amplification primer which comprises the relevant non-natural/modified nucleotide, then it is essential in this embodiment that the non-natural/modified nucleotide is capable of being copied by the polymerase used for the amplification reaction.

In one embodiment, the double-stranded nucleic acid molecules to be cleaved may be exposed to a mixture containing the appropriate glycosylase (to generate the abasic site) and one or more suitable endonucleases (to subsequently cleave). In such mixtures the glycosylase and the endonuclease will typically be present in an activity ratio of at least about 2:1.

Cleavage of double stranded nucleic acids at pre-determined abasic sites has particular advantages in relation to the creation of templates for nucleic acid sequencing. In particular, cleavage at an abasic site generated by treatment with a glycosylase such as UDG generates a free 3' hydroxyl group on the cleaved strand which can provide an initiation point for sequencing a region of the complementary strand. Moreover, if the starting double-stranded nucleic acid contains only one cleavable base (e.g. uracil) on one strand then a single "nick" can be generated at a unique position in this strand of the duplex. Since the cleavage reaction requires a residue, e.g. deoxyuridine, which does not occur naturally in DNA, but is otherwise independent of sequence context, if only one non-natural base is included there is no possibility of glycosylase-mediated cleavage occurring elsewhere at unwanted positions in the duplex. In contrast, were the double-stranded nucleic acid to be cleaved with a "nicking" endonuclease that recognises a specific sequence, there is a possibility that the enzyme may create nicks at other sites in the duplex (in addition to the desired cleavage site) if these possess the correct recognition sequence. This could present a problem if nicks are created in the strand it is intended to sequence rather than the strand that will be fully or partially removed to create the sequencing template and is a particular risk if the target portion of the double-stranded nucleic acid molecule is of unknown sequence.

The fact that there is no requirement for the non-natural residue (e.g. uracil) to be located in a detailed sequence context in order to provide a site for cleavage using this approach is itself advantageous. In particular, if the cleavage site is to be incorporated into an amplification primer to be used in the production of a clustered array by solid-phase amplification, it is necessary only to replace one natural nucleotide in the primer (e.g. T) with a non-natural nucleotide (e.g. U) in order to enable cleavage at a pre-determined cleavage site. There is no need to engineer the primer to include a restriction enzyme recognition sequence of several nucleotides in length. Oligonucleotide primers including U nucleotides, and the other non-natural nucleotides listed above, can easily be prepared using conventional techniques and apparatus for chemical synthesis of oligonucleotides.

Another advantage gained by cleavage of abasic sites in a double-stranded molecule generated by action of UDG on uracil is that the first base incorporated in a "sequencing-by-synthesis" reaction initiating at the free 3' hydroxyl group formed by cleavage at such a site will always be T. Hence, if the double-stranded nucleic acid molecule forms part of a clustered array comprised of many such molecules, all of which are cleaved in this manner to produce sequencing templates, then the first base universally incorporated across the whole array will be T. This can provide a sequence-independent assay for cluster intensity at the start of a sequencing "run".

iii) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a pre-determined site for cleavage using a chemical agent capable of selectively cleaving the phosphodiester bond between a deoxyribonucleotide and a ribonucleotide or using a ribonuclease (RNAse). Therefore, the invention also encompasses production of sequencing templates by cleavage of one strand (of a double-stranded nucleic acid molecule) at a site containing one or more consecutive ribonucleotides using such a chemical cleavage agent or an RNase. Preferably the strand to be cleaved contains a single ribonucleotide to provide a pre-determined site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimise chemical (or enzymatic) cleavage. By way of example, rUMP or rCMP are generally preferred if cleavage is to be carried out by exposure to metal ions, especially rare earth metal ions.

The ribonucleotide(s) will typically be incorporated into one strand of the double-stranded nucleic acid molecule, and may be situated in a region thereof which is single-stranded when the two complementary strands of the double-stranded molecule are annealed (i.e. in a 5' overhanging portion). In particular, if the double-stranded nucleic acid molecule is prepared by solid-phase PCR amplification using forward and reverse amplification primers, one of which contains at least one ribonucleotide, the standard DNA polymerase enzymes used for PCR amplification are not capable of copying ribonucleotide templates. Hence, the products of the solid-phase PCR reaction will contain an overhanging 5' region comprising the ribonucleotide(s) and any remainder of the amplification primer upstream of the ribonucleotide(s).

The phosphodiester bond between a ribonucleotide and a deoxyribonucleotide, or between two ribonucleotides can also be cleaved by an RNase. Any endocytic ribonuclease of appropriate substrate specificity can be used for this purpose. If the ribonucleotide(s) are present in a region which is single-stranded when the two complementary strands of the double-stranded molecule are annealed (i.e. in a 5' overhanging portion), then the RNase will be an endonuclease which has specificity for single strands containing ribonucleotides. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesised using standard techniques for oligonucleotide chemical synthesis with appropriate ribonucleotide precursors. If the double-stranded nucleic acid molecule is prepared by solid-phase nucleic acid amplification, then it is convenient to incorporate one or more ribonucleotides into one of the primers to be used for the amplification reaction.

iv) Photochemical Cleavage

The term "photochemical cleavage" encompasses any method which utilises light energy in order to achieve cleavage of one or both strands of the double-stranded nucleic acid molecule.

A pre-determined site for photochemical cleavage can be provided by a non-nucleotide chemical spacer unit in one of the strands of the double-stranded molecule. Suitable photochemical cleavable spacers include the PC spacer phosphoamidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

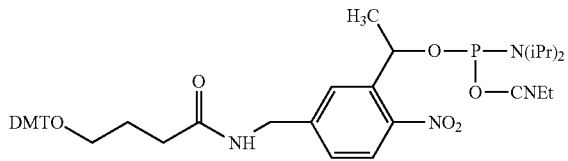

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable double-stranded nucleic acid molecule by solid-phase amplification.

v) Cleavage of Hemimethylated DNA

Site-specific cleavage of one strand of a double-stranded nucleic acid molecule may also be achieved by incorporating one or more methylated nucleotides into this strand and then cleaving with an endonuclease enzyme specific for a recognition sequence including the methylated nucleotide(s).

The methylated nucleotide(s) will typically be incorporated in a region of one strand of the double-stranded nucleic acid molecule having a complementary stretch of non-methylated deoxyribonucleotides on the complementary strand, such that annealing of the two strands produces a hemimethylated duplex structure. The hemimethylated duplex may then be cleaved by the action of a suitable endonuclease. For the avoidance of doubt, enzymes which cleave such hemimethylated target sequences are not to be considered as "restriction endonucleases" excluded from the scope of the second aspect of the invention, but rather are intended to form part of the subject-matter of the invention.

Polynucleotides incorporating one or methylated nucleotides may be prepared using standard techniques for automated DNA synthesis, using appropriately methylated nucleotide precursors. If the double-stranded nucleic acid molecule is prepared by solid-phase nucleic acid amplification, then it is convenient to incorporate one or more methylated nucleotides into one of the primers to be used for the amplification reaction.

vi) PCR Stoppers

In another embodiment of the invention the double-stranded nucleic acid may be prepared by solid-phase amplification using forward and reverse primers, one of which contains a "PCR stopper". A "PCR stopper" is any moiety (nucleotide or non-nucleotide) which prevents read-through of the polymerase used for amplification, such that it cannot copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e. it may simply be a stretch of single-stranded DNA. The molecule may then be cleaved in the 5' overhanging region with the use of a cleavage reagent (e.g. an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Va., USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g. exposure to alkali) or an enzyme (e.g. AP-endonuclease VI, Shida et al. Nucleic Acids Research, 1996, Vol. 24, 4572-4576).

vii) Cleavage of Peptide Linker

A cleavage site can also be introduced into one strand of the double-stranded nucleic molecule by preparing a conjugate structure in which a peptide molecule is linked to one strand of the nucleic acid molecule. The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the double-stranded nucleic acid molecule, with the peptide portion being conjugated to the 5' end of this strand, adjacent to the point of attachment to the solid surface. If the double-stranded nucleic acid is prepared by solid-phase amplification, the peptide conjugate may be incorporated at the 5' end of one of the amplification primers. Obviously the peptide component of this primer will not be copied during PCR amplification, hence the "bridged" amplification product will include a cleavable 5' peptide "overhang" on one strand.

Conjugates between peptides and nucleic acids wherein the peptide is conjugated to the 5' end of the nucleic acid can be prepared using techniques generally known in the art. In one such technique the peptide and nucleic acid components of the desired amino acid and nucleotide sequence can be synthesised separately, e.g. by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-5-tert-butylsulfenyl-l-cysteinyl)aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the Modified Peptide is converted to the thiophenyl analogue by the use of thiophenol, whilst the Modified Oligonucleotide is reduced using the tris(carboxyethyl)phosphine. Coupling of these two intermediates, followed by the "native ligation" step, leads to formation of the Oligonucleotide-Peptide Conjugate.

The conjugate strand containing peptide and nucleic acid can be covalently attached to a solid support using any suitable covalent linkage technique known in the art which is compatible with the chosen surface. For example, covalent attachment to a solid supported polyacrylamide hydrogel surface can be achieved by inclusion of a thiophosphate group on the "free" end of the peptide component (i.e. the end not conjugated to the nucleic acid). If the peptide/nucleic acid conjugate structure is an amplification primer to be used for solid-phase PCR amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase PCR, then its length and nucleotide sequence will be selected to enable annealing to the template to be amplified.

Denaturation

In all embodiments of the invention, regardless of the method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols (Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template.

In other embodiments of the invention, sequencing can be initiated directly after the cleavage step with no need for denaturation to remove a portion of the cleaved strand(s). If the cleavage step generates a free 3' hydroxyl group on one cleaved strand still hybridised to a complementary strand then sequencing can proceed from this point using a strand-displacement polymerase enzyme without the need for an initial denaturation step. In particular, strand displacement sequencing may be used in conjunction with template generation by cleavage with nicking endonucleases, or by hydrolysis of an abasic site with endonuclease, heat or alkali treatment.

Features of Solid Supports

In all embodiments of the invention, the term "solid support", as used herein, refers to the material to which the polynucleotides molecules are attached. Suitable solid supports are available commercially, and will be apparent to the skilled person. The supports can be manufactured from materials such as glass, ceramics, silica and silicon. Supports with a gold surface may also be used. The supports usually comprise a flat (planar) surface, or at least a structure in which the polynucleotides to be interrogated are in approximately the same plane. Alternatively, the solid support can be non-planar, e.g., a microbead. Any suitable size may be used. For example, the supports might be on the order of 1-10 cm in each direction.

The first aspect of the invention relates to generation of sequencing templates on a particular type of surface, namely solid supported polyacrylamide hydrogels.

As aforesaid, in preparing hydrogel-based solid-supported molecular arrays, a hydrogel is formed and molecules displayed from it. These two features—formation of the hydrogel and construction of the array—may be effected sequentially or simultaneously.

Where the hydrogel is formed prior to formation of the array, it is typically produced by allowing a mixture of comonomers to polymerise. Generally, the mixture of comonomers contain acrylamide and one or more comonomers, the latter of which permit, in part, subsequent immobilisation of molecules of interest so as to form the molecular array.

The comonomers used to create the hydrogel typically contain a functionality that serves to participate in crosslinking of the hydrogel and/or immobilise the hydrogel to the solid support and facilitate association with the target molecules of interest.

Generally, as is known in the art, polyacrylamide hydrogels are produced as thin sheets upon polymerisation of aqueous solutions of acrylamide solution. A multiply unsaturated (polyunsaturated) crosslinking agent (such as bisacrylamide) is generally present; the ratio of acrylamide to bisacrylamide is generally about 19:1. Such casting methods are well known in the art (see for example Sambrook et al., 2001, *Molecular Cloning, A Laboratory Manual*, 3rd Ed, Cold Spring Harbor Laboratory Press, Cold Spring Harbor Laboratory Press, NY) and need not be discussed in detail here.

Some form of covalent surface modification of the solid support may be practiced in order to achieve satisfactory immobilisation of either hydrogel-based molecular arrays or hydrogels to which it is desired to array molecules. However, the inventors have observed that such functional modification of the support is not necessary in order to achieve satisfactory immobilisation of arrays of polynucleotides. In order to make useful supported arrays capable of binding molecules of interest, a mixture of comonomers comprising at least one hydrophilic monomer and a functionalised comonomer (functionalised to the extent that the monomer once incorporated into the polymer is capable of binding the molecule of interest to the surface of the hydrogel) may be polymerised so as to form a hydrogel capable of being immobilised on a solid supported, preferably a silica-based, substrate. In particular, the hydrogel may be substantially free of any binder silane components.

In one embodiment the hydrogel may be formed by a method comprising polymerising on said support a mixture of:

(i) a first comonomer which is acrylamide, methacrylamide, hydroxyethyl methacrylate or N-vinyl pyrrolidinone; and (ii) a second comonomer which is a functionalised acrylamide or acrylate of formula (I):

$$H_2C=C(H)—C(=O)-A-B—C \qquad (I);$$

or a methacrylate or methacrylamide of formula (II):

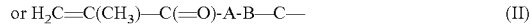

$$\text{or } H_2C=C(CH_3)—C(=O)-A-B—C— \qquad (II)$$

(wherein:

A is NR or O, wherein R is hydrogen or an optionally substituted saturated hydrocarbyl group comprising 1 to 5 carbon atoms;

—B— is an optionally substituted alkylene biradical of formula —(CH$_2$)$_n$— wherein n is an integer from 1 to 50; and wherein n=2 or more, one or more optionally substituted ethylene biradicals —CH$_2$CH$_2$— of said alkylene biradical may be independently replaced by ethenylene and ethynylene moieties; and wherein n=1 or more, one or more methylene biradicals —CH$_2$— may be replaced independently with an optionally substituted mono- or polycyclic hydrocarbon biradical comprising from 4 to 50 carbon atoms, or a corresponding heteromonocyclic or heteropolycyclic biradical wherein at least 1 CH$_2$ or CH$_2$ is substituted by an oxygen sulfur or nitrogen atom or an NH group; and C is a group for reaction with a compound to bind said compound covalently to said hydrogel) to form a polymerised product, characterised in that said method is conducted on, and immobilizes the polymerised product to, said support which is not covalently surface-modified.

It has been found that omission of a covalent surface-modification step (particularly of the solid support) affords a surface having greater passivity than in the prior art, particularly when compared to those instances where the use of the silane-modifying agents described above with silica-based substrates are employed.

The solid upon which the hydrogel is supported is not limited to a particular matrix or substrate. Suitable supports include silica-based substrates, such as glass, fused silica and other silica-containing materials; they may also be silicone hydrides or plastic materials such as polyethylene, polystyrene, poly(vinyl chloride), polypropylene, nylons, polyesters, polycarbonates and poly(methyl methacrylate). Preferred plastics material are poly(methyl methacrylate), polystyrene and cyclic olefin polymer substrates. Alternatively, other solid supports may be used such as gold, titanium dioxide, or silicon supports. The foregoing lists are intended to be illustrative of, but not limited to, the invention. Preferably, the support is a silica-based material or plastics material such as discussed herein.

The methods by which the mixture of comonomers are polymerised in the invention are not characteristic of this invention and will be known to the skilled person (e.g. by recourse to Sambrook et al. (supra). Generally, however, the polymerisation will be conducted in an aqueous medium, and polymerisation initiated by any suitable initiator. Potassium or ammonium persulfate as an initiator is typically employed. Tetramethylethylenediamine (TMEDA or TEMED) may be and generally is used to accelerate the polymerisation.

It is not necessary that, a polyunsaturated crosslinking agent such as bisacrylamide or pentaerythritol tetraacrylate is present in the mixture which is polymerised; nor is it necessary to form PRP-type intermediates and crosslink them.

Generally, in producing hydrogels according to this invention, only one compound of formulae (I) or (II) will be used.

Use of a compound of the formulae (I) or (II) permits formation of a hydrogel capable of being immobilised to solid supports, preferably silica-based solid supports. The compounds of these formulae comprise portions A, B and C as defined herein.

Biradical A may be oxygen or N(R) wherein R is hydrogen or a $C_{1-5}$ alkyl group. Preferably, R is hydrogen or methyl, particularly hydrogen. Where R is a $C_{1-5}$ alkyl group, this may contain one or more, e.g. one to three substituents. Preferably, however, the alkyl group is unsubstituted.

Biradical B is a predominantly hydrophobic linking moiety, connecting A to C and may be an alkylene biradical of formula —$(CH_2)_n$—, wherein n is from 1 to 50. Preferably n is 2 or more, e.g. 3 or more. Preferably n is 2 to 25, particularly 2 to 15, more particularly 4 to 12, for example 5 to 10.

Where n in —$(CH_2)_n$— is 2 or more, one or more biradicals —$CH_2CH_2$— (-ethylene-) may be replaced with ethenylene or ethynylene biradicals. Preferably, however, the biradical B does not contain such unsaturation.

Additionally, or alternatively, where n in —$(CH_2)_n$— is 1 or more, one or more methylene radicals —$CH_2$— in B may be replaced with a mono- or polycyclic biradical which preferably comprises 5 to 10 carbon atoms e.g. 5 or 6 carbon atoms. Such cyclic biradicals may be, for example, 1,4-, 1,3- or 1,2-cyclohexyl biradicals. Bicyclic radicals such as napthyl or decahydronaphthyl may also be employed. Corresponding heteroatom-substituted cyclic biradicals to those homocyclic biradicals may also be employed, for example pyridyl, piperidinyl, quinolinyl and decahydroquinolinyl.

It will be appreciated that the scope of —B— is thus not particularly restricted. Most preferably, however, —B— is a simple, unsubstituted, unsaturated alkylene biradical such as a $C_3$-$C_{10}$ alkylene group, optimally $C_5$-$C_8$, such as n-pentylene: —$(CH_2)_5$—.

Where an alkyl group (or alkylene, alkenylene etc) is indicated as being (optionally) substituted, substituents may be selected from the group comprising hydroxyl, halo (i.e. bromo, chloro, fluoro or iodo), carboxyl, aldehydro, amine and the like. The biradical —B— is preferably unsubstituted or substituted by fewer than 10, preferably fewer than 5, e.g. by 1, 2 or 3 such substituents.

Group C serves to permit attachment of molecules of interest after formation of the hydrogel. The nature of Group C is thus essentially unlimited provided that it contains a functionality allowing reaction between the hydrogel and the molecules to be immobilised. Preferably, such a functionality will not require modification prior to reaction with the molecule of interest and thus the C group is ready for direct reaction upon formation of the hydrogel. Preferably such a functionality is a hydroxyl, thiol, amine, acid (e.g. carboxylic acid), ester and haloacetamido, haloacetamido and in particular bromoacetamido being particularly preferred. Other appropriate C groups will be evident to those skilled in the art and include groups comprising a single carbon-carbon double bond which is either terminal (i.e. where a C group has an extremity terminating in a carbon-carbon double bond) or where the carbon-carbon double bond is not at a terminal extremity. When a C group comprises a carbon-carbon double bond, this is preferably fully substituted with $C_{1-5}$ alkyl groups, preferably methyl or ethyl groups, so that neither carbon atom of the C=C moiety bears a hydrogen atom.

The C moiety may thus comprise, for example, a dimethylmaleimide moiety as disclosed in U.S. Pat. No. 6,372,813, WO01/01143, WO02/12566 and WO03/014394.

The (meth)acrylamide or (meth)acrylate of formula (I) or (II) which is copolymerised with acrylamide, methacrylamide, hydroxyethyl methacrylate or N-vinyl pyrrolidinone is preferably an acrylamide or acrylate, i.e. of formula (I). More preferably it is an acrylamide and still more preferably it is an acrylamide in which A is NH.

The reaction between a comonomer of formula (I) or (II) and acrylamide, methacrylamide, hydroxyethyl methacrylate or N-vinyl pyrrolidinone methacrylamide, particularly acrylamide, has been found to afford hydrogels particularly suitable for use in the generation of molecular arrays. However, it will be appreciated by those skilled in the art that analogous copolymers may be formed by the reaction between comonomers of formula (I) or (II) and any vinylogous comonomer, hydroxyethylmethacrylate and n-vinyl pyrrolidinone being two examples of such vinylogous comonomers.

Control of the proportion of monomer of formula (I) or (II) to that of the first comonomer (e.g. acrylamide and/or methacrylamide, preferably acrylamide) allows adjustment of the physical properties of the hydrogel obtained on polymerisation. It is preferred that the comonomer of formula (I) or (II) is present in an amount of ≥1 mol %, preferably ≥2 mol % (relative to the total molar quantity of comonomers) in order for the hydrogel to have optimum thermal and chemical stability under conditions typically encountered during the preparation, and subsequent manipulation, of the molecular arrays produced from the hydrogels. Preferably, the amount of comonomer of formula (I) or (II) is less than or equal to about 5 mol %, more preferably less than or equal to about 4 mol %. Typical amounts of comonomer of formula (I) or (II) used are 1.5-3.5 mol %, exemplified herein by about 2% and about 3%.

The amounts of acrylamide or methacrylamide from which the hydrogels are primarily constructed are those typically used to form hydrogels, e.g. about 1 to about 10% w/v, preferably less than 5 or 6% w/v, e.g. about 1 to about 2% w/v. Again, of course, the precise nature of the hydrogel may be adjusted by, in part, control of the amount of acrylamide or methacrylamide used.

When forming the hydrogels, acrylamide or methacrylamide may be dissolved in water and mixed with a solution of a comonomer of formula (I) or (II). The latter may be conveniently dissolved in a water-miscible solvent, such as dimethylformamide (DMF), or water itself. The most appropriate solvent may be selected by the skilled person and shall depend upon the structure of the comonomer of formula (I) or (II).

The methods by which the monomers of formula (I) or (II) are synthesised will be evident to those skilled in the art. By way of example, the synthesis of a particularly preferred monomer (of formula (I) wherein A=NH, —B—=—$(CH_2)_5$— and —C=—N(H)—C(=O)$CH_2$Br is provided as an example hereinafter.

As noted above, the general methods by which the polymerisation is carried out are known to those skilled in the art. For example, generally acrylamide or methacrylamide is dissolved in purified water (e.g. Milli Q) and potassium or ammonium persulfate dissolved separately in purified water. The comonomer of formula (I) or (II) may be conveniently dissolved in a water-miscible organic solvent, e.g. glycerol, ethanol, methanol, dimethylformamide (DMF) etc. TEMED may be added as appropriate. Once formulated (a typical preparation is described in the examples), the mixture is polymerised with as little delay as possible after its formulation.

The polymerisation process may be conducted by any convenient means.

The second aspect of the invention is not limited with respect to the nature of the solid support and can be used in conjunction with essentially any type of support known in the art for production of polynucleotide arrays, and more specifically with any type of support which is compatible with solid-phase nucleic acid amplification. Suitable supports include those coated with functionalised silanes. In particular, the method of the second aspect of the invention can be used in conjunction with the silane-coated solid supports described in WO 98/44151 and WO 00/18957.

Construction of Arrays by Solid Phase Amplification

In a particular embodiment of the invention, the methods according to the first and second aspects of the invention may be used to prepare templates for sequencing starting from double-stranded nucleic acid molecules present in clustered arrays of nucleic acid colonies generated by solid-phase nucleic acid amplification. In this context, the term "solid-phase amplification" refers to an amplification reaction which is analogous to standard PCR, except that the forward and reverse amplification primers are immobilised (e.g. covalently attached) to a solid support at or near the 5' end. The products of the PCR reaction are thus extended strands derived by extension of the amplification primers that are immobilised on the solid support at or near the 5' end. Solid-phase amplification may itself be carried out, for example, using procedures analogous to those described in WO 98/44151 and WO 00/18957, the contents of which are incorporated herein in their entirety by reference.

As a first step in colony generation by solid-phase amplification a mixture of forward and reverse amplification primers may be immobilised or "grafted" onto the surface of a suitable solid support. The grafting step will generally involve covalent attachment of the primers to the support at or near the 5' end, leaving the 3' end free for primer extension.

The amplification primers are typically oligonucleotide molecules have the following structures:
Forward primer: A-L-S1
Reverse primer: A-L-S2

Wherein A represents a moiety which allows attachment to a solid support, L represents an optional linker moiety and S1 and S2 are polynucleotide sequences which permit amplification of a substrate nucleic acid molecule comprising a target region that it is desired to (fully or partially) sequence.

The mixture of primers grafted onto the solid support will generally comprise substantially equal amounts of the forward and reverse primers.

Group A can be any moiety (including a non-nucleotide chemical modification) which enables attachment (preferably covalent) to a solid support. In all aspects of the invention group A may comprise a sulphur-containing nucleophile, such as phosphorothioate, present at the 5' end of a polynucleotide strand. The most preferred means of grafting primers to a solid support is via 5' phosphorothioate attachment to a hydrogel comprised of polymerised acrylamide and N-(5-bromoacetamidylpentyl)acrylamide (BRAPA).

L represents a linker or spacer which may be included but is not strictly necessary. The linker may be included in order to ensure that a cleavage site present in the immobilised polynucleotide molecules generated as a result of the amplification reaction is positioned at an optimum distance from the solid support, or the linker may itself contain a cleavage site.

The linker may be a carbon-containing chain such as those of formula $(CH_2)_n$ wherein "n" is from 0.1 to about 1500, for example less than about 1000, preferably less than 100, e.g. from 2-50, particularly 5-25. However, a variety of other linkers may be employed with the only restriction placed on their structures being that the linkers are stable under conditions under which the polynucleotides are intended to be used subsequently, e.g. conditions used in DNA amplification, cleavage and sequencing.

Linkers which do not consist of only carbon atoms may also be used. Such linkers include polyethylene glycol (PEG) having a general formula of $(CH_2-CH_2-O)_m$, wherein m is from about 1 to 600, preferably less than about 500.

Linkers formed primarily from chains of carbon atoms and from PEG may be modified so as to contain functional groups which interrupt the chains. Examples of such groups include ketones, esters, amines, amides, ethers, thioethers, sulfoxides, sulfones. Separately or in combination with the presence of such functional groups may be employed alkene, alkyne, aromatic or heteroaromatic moieties, or cyclic aliphatic moieties (e.g. cyclohexyl). Cyclohexyl or phenyl rings may, for example, be connected to a PEG or $(CH_2)_n$ chain through their 1- and 4-positions.

As an alternative to the linkers described above, which are primarily based on linear chains of saturated carbon atoms, optionally interrupted with unsaturated carbon atoms or heteroatoms, other linkers may be envisaged which are based on nucleic acids or monosaccharide units (e.g. dextrose). It is also within the scope of this invention to utilise peptides as linkers.

In a further embodiment the linker may comprise one or more nucleotides. Such nucleotides may also be referred to herein as "spacer" nucleotides. Typically from 1 to 20, more preferably from 1 to 15 or from 1 to 10, and more particularly 2, 3, 4, 5, 6, 7, 8, 9 or 10 spacer nucleotides may be included. Most preferably the primer will include 10 spacer nucleotides. It is preferred to use polyT spacers, although other nucleotides and combinations thereof can be used. In one preferred embodiment the primer may include 10T spacer nucleotides.

For the primer grafting reaction to proceed a mixture of the amplification primers is applied to a solid support under conditions which permit reaction between moiety A and the support. The solid support may be suitably functionalised to permit covalent attachment via moiety A. The result of the grafting reaction is a substantially even distribution of the primers over the solid support.

In certain embodiments the template to be amplified may be grafted onto the solid support together with the amplification primers in a single grafting reaction. This can be achieved by adding template molecules including moiety A at the 5' end to the mixture of primers to form a primer-template mixture. This mixture is then grafted onto the solid support in a single step. Amplification may then proceed using the immobilised template and primers in a reaction analogous to that described in WO 00/18957. The first step in such a reaction will be hybridisation between surface-bound templates and surface-bound amplification primers.

If a mixture of primers only is grafted onto the solid support, the template to be amplified may be added in free solution. The amplification reaction may then proceed substantially as described in WO 98/44151. Briefly, following attachment of the primers the solid support is contacted with the template to be amplified under conditions which permit hybridisation between the template and the immobilised primers. The template is usually added in free solution under suitable hybridisation conditions, which will be apparent to the skilled reader. Typically hybridisation conditions are, for example, 5×SSC at 40° C., following an initial denaturation step. Solid-phase amplification can then proceed, the first step of the amplification being a primer extension step in which nucleotides are added to the 3' end of the immobilised primer hybridised to the template to produce a fully extended complementary strand. This complementary strand will thus include at its 3' end a sequence which is capable of binding to the second primer molecule immobilised on the solid support.

Further rounds of amplification (analogous to a standard PCR reaction) lead to the formation of clusters or colonies of template molecules bound to the solid support.

Sequences S1 and S2 in the amplification primers may be specific for a particular target nucleic acid that it is desired to amplify, but in other embodiments sequences S1 and S2 may be "universal" primer sequences which enable amplification of any target nucleic acid of known or unknown sequence which has been modified to enable amplification with the universal primers.

Suitable substrates to be amplified with universal primers may be prepared by modifying polynucleotides comprising the target region to be amplified (and sequenced) by addition of known adaptor sequences to the 5' and 3' ends of the target polynucleotides to be amplified. The target molecules themselves may be any double-stranded polynucleotide molecules it is desired to sequence (e.g. random fragments of human genomic DNA). The adaptor sequences enable amplification of these molecules on a solid support to form clusters using forward and reverse primers having the general structure described above, wherein sequences S1 and S2 are universal primer sequences.

The adaptors are typically short oligonucleotides that may be synthesised by conventional means. The adaptors may be attached to the 5' and 3' ends of target nucleic acid fragments by a variety of means (e.g. subcloning, ligation. etc). More specifically, two different adaptor sequences are attached to a target nucleic acid molecule to be amplified such that one adaptor is attached at one end of the target nucleic acid molecule and another adaptor is attached at the other end of the target nucleic acid molecule. The resultant construct comprising a target nucleic acid sequence flanked by adaptors may be referred to herein as a "substrate nucleic acid construct". The target polynucleotides may advantageously be size-fractionated prior to modification with the adaptor sequences.

The adaptors contain sequences which permit nucleic acid amplification using the amplification primer molecules immobilised on the solid support. These sequences in the adaptors may be referred to herein as "primer binding sequences". In order to act as a template for nucleic acid amplification, a single strand of the template construct must contain a sequence which is complementary to sequence S1 in the forward amplification primers (such that the forward primer molecule can bind and prime synthesis of a complementary strand) and a sequence which corresponds to sequence S2 in the reverse amplification primer molecules (such that the reverse primer molecule can bind to the complementary strand). The sequences in the adaptors which permit hybridisation to primer molecules will typically be around 20-40 nucleotides in length, although the invention is not limited to sequences of this length.

The precise identity of sequences S1 and S2 in the amplification primers, and hence the cognate sequences in the adaptors, are generally not material to the invention, as long as the primer molecules are able to interact with the amplification sequences in order to direct PCR amplification. The criteria for design of PCR primers are generally well known to those of ordinary skill in the art.

Solid-phase amplification by either the method analogous to that of WO 98/44151 or that of WO 00/18957 will result in production of a clustered array comprised of colonies of "bridged" amplification products. Both strands of the amplification products will be immobilised on the solid support at or near the 5' end, this attachment being derived from the original attachment of the amplification primers. Typically the amplification products within each colony will be derived from amplification of a single template (target) molecule.

Modifications required to enable subsequent cleavage of the bridged amplification products may be advantageously included in one or both amplification primers. Such modifications may be placed anywhere in the amplification primer, provided this does not affect the efficiency of the amplification reaction to a material extent. Thus, the modifications which enable cleavage may form part of the linker region L or one or both of sequences S1 or S2. By way of example, the amplification primers may be modified to include inter alia diol linkages, uracil nucleotides, ribonucleotides, methylated nucleotides, peptide linkers, PCR stoppers or recognition sequences for a restriction endonuclease. Because all nucleic acid molecules prepared by solid-phase amplification will ultimately contain sequences derived from the amplification primers, any modifications in the primers will be carried over into the amplified products.

Therefore, in a further aspect the invention provides a method of solid-phase nucleic acid amplification wherein forward and reverse amplification primers covalently attached to a solid support at the 5' end are used to amplify one or more polynucleotide templates, the method being characterised in that one or both of the amplification primers includes a site for cleavage by a method other than digestion with the restriction endonuclease or a nicking endonuclease.

Preferred features of the amplification primers are as described above and preferred cleavage methods are as described above in connection with the first and second aspects of the invention. Other preferred features described in relation to the first and second aspects of the invention apply mutatis mutandis to this aspect of the invention.

The utility of the "template formation" method of the first and second aspects of the invention is not limited to formation of templates from double-stranded nucleic acids produced by an amplification reaction, although this is preferred. The method may be applied to linearisation of immobilised double-stranded polynucleotides produced on a support by any other means.

Methods of Sequencing

The invention also encompasses method of sequencing nucleic acid templates generated using the methods of the invention. Thus, the invention provides a method of nucleic acid sequencing comprising forming a template for nucleic acid sequencing using a method according to the first or second aspect of the invention and performing a nucleic acid sequencing reaction to determine the sequence one at least one region of the template.

Sequencing can be carried out using any suitable "sequencing-by-synthesis" technique, wherein nucleotides are added successively to a free 3' hydroxyl group, resulting in synthesis of a polynucleotide chain in the 5' to 3' direction. The nature of the nucleotide added is preferably determined after each addition.

An initiation point for a sequencing reaction may be provided by annealing of a sequencing primer to a single-stranded region of the template. Thus, the invention encompasses methods wherein the nucleic acid sequencing reaction comprises hybridising a sequencing primer to a single-stranded region of the template generated in step (iii) of the "template generation" method of the first or second aspect of the invention, sequentially incorporating one or more nucleotides into a polynucleotide strand complementary to the region of the template to be sequenced, identifying the base present in one or more of the incorporated nucleotide(s) and thereby determining the sequence of a region of the template.

In other embodiments of the invention the initiation point for the sequencing reaction may be a free 3' hydroxyl group generated by cleavage of one strand of the template itself (e.g.

by cleavage of an abasic nucleotide with endonuclease, heat or alkali). Thus, the invention also provides methods of sequencing which involve forming a template for nucleic acid sequencing using a method comprising steps (i) and (ii) only of the "template formation" methods of the first or second aspects of the invention, carrying out a strand displacement sequencing reaction by sequentially adding one or more nucleotides to a free 3' hydroxyl group generated on the strand cleaved in step (ii), identifying the base present in one or more of the incorporated nucleotide(s) and thereby determining the sequence of a region of the template.

A preferred sequencing method which can be used in all aspects of the invention relies on the use of modified nucleotides containing 3' blocking groups that can act as chain terminators. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label to facilitate their detection. Preferably this is a fluorescent label. Each nucleotide type may carry a different fluorescent label. However the detectable label need not be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means.

The methods of the invention are not limited to use of the sequencing method outlined above, but can be used in conjunction with essentially any sequencing methodology which relies on successive incorporation of nucleotides into a polynucleotide chain. Suitable techniques include, for example, Pyrosequencing™, FISSEQ (fluorescent in situ sequencing), MPSS (massively parallel signature sequencing) and sequencing by ligation-based methods.

The target polynucleotide to be sequenced using the method of the invention may be any polynucleotide that it is desired to sequence. The target polynucleotide may be of known, unknown or partially known sequence, for example in re-sequencing applications. Using the template preparation method described in detail herein it is possible to prepare templates starting from essentially any double-stranded target polynucleotide of known, unknown or partially known sequence. With the use of arrays it is possible to sequence multiple targets of the same or different sequence in parallel. A particularly preferred application of the method is in the sequencing of fragments of genomic DNA.

The invention will be further understood with reference to the following non-limiting experimental examples.

BACKGROUND

The use of diol within DNA or oligonucleotides has been widely reported in the literature as a cleavable linker or as masked aldehyde functionality and used for diverse applications as mutagenesis (Karion et al. (2001) Nucl. Acids Res. 29(12), 2456-2463), enzyme mechanism study (Brevnov M. G. et al. (1997) Nucl. Acids Res. 25(16), 3302-3309), post-synthesis modifications of oligonucleotides (Ollivier N. et al. (2002) Tet. Lett. 43, 997-999) or new solid support for peptide automated synthesis (Melnyk O. et al. (2001) J. Org. Chem. 66(12), 4153-4160). The deprotection method has been proven compatible with DNA integrity.

General Methods

The following are general methods used in the accompanying examples

Acrylamide Coating of Glass Chips

The solid supports used in this experiment were 8-channel glass chips such as those provided by Micronit (Twente, Nederland) or IMT (Neuchâtel, Switzerland). However, the experimental conditions and procedures are readily applicable to other solid supports.

Chips were washed as follows: neat Decon for 30 min, milliQ $H_2O$ for 30 min, NaOH 1N for 15 min, milliQ $H_2O$ for 30 min, HCl 0.1N for 15 min, milliQ $H_2O$ for 30 min.

Polymer Solution Preparation

For 10 ml of 2% polymerisation mix.
10 ml of 2% solution of acrylamide in milliQ H2O
165 µl of a 100 mg/ml N-(5-bromoacetamidylpentyl)acrylamide (BRAPA) solution in DMF (23.5 mg in 235 µl DMF)
11.5 µl of TEMED
100 µl of a 50 mg/ml solution of potassium persulfate in milliQ $H_2O$ (20 mg in 400 µl $H_2O$)

The 10 ml solution of acrylamide was first degassed with argon for 15 min. The solutions of BRAPA, TEMED and potassium persulfate were successively added to the acrylamide solution. The mixture was then quickly vortexed and immediately used. Polymerization was then carried out for 1 h 30 at RT. Afterwards the channels were washed with milliQ $H_2O$ for 30 min. The slide was then dried by flushing argon through the inlets and stored under low pressure in a dessicator.

Synthesis of
N-(5-bromoacetamidylpentyl)acrylamide (BRAPA)

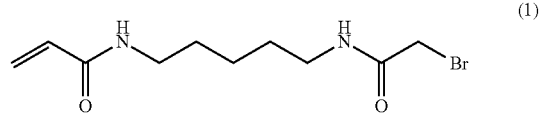

(1)

N-Boc-1,5-diaminopentane toluene sulfonic acid was obtained from Novabiochem. The bromoacetyl chloride and acryloyl chloride were obtained from Fluka. All other reagents were Aldrich products.

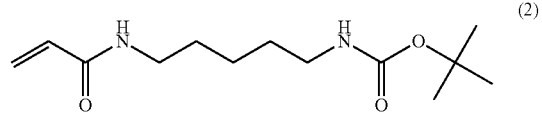 [SMILES: C=CC(=O)NCCCCCNC(=O)OC(C)(C)C]

(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether:ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, d$_6$-DMSO): 1.20-1.22 (m, 2H, CH$_2$), 1.29-1.43 (m, 13H, tBu, 2×CH$_2$), 2.86 (q, 2H, J=6.8 Hz and 12.9 Hz, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C$_{13}$H$_{24}$N$_2$O$_3$ 256. found 279 (256+Na$^+$).

(3)

$$\text{CH}_2=\text{CH-C(O)-NH-(CH}_2\text{)}_5\text{-NH}_3^+\text{CF}_3\text{COO}^-$$

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D$_2$O): 1.29-1.40 (m, 2H, CH$_2$), 1.52 (quint., 2H, J=7.1 Hz, CH$_2$), 1.61 (quint., 2H, J=7.7 Hz, CH$_2$), 2.92 (t, 2H, J=7.6 Hz, CH$_2$), 3.21 (t, 2H, J=6.8 Hz, CH$_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for C$_8$H$_{16}$N$_2$O 156. found 179 (156+Na$^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, d$_6$-DMSO): 1.21-1.30 (m, 2H, CH$_2$), 1.34-1.48 (m, 4H, 2×CH$_2$), 3.02-3.12 (m, 4H, 2×CH$_2$), 3.81 (s, 2H, CH$_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for C$_{10}$H$_{17}$BrN$_2$O$_2$ 276 or 278. found 279 (278+H$^+$), 299 (276+Na$^+$).

Grafting of Primers

The primers were 5'-phosphorothioate oligonucleotides. Their sequences and suppliers varied according to the experiment they were used for (see specific examples).

Grafting was carried out using 80 μl per channel in 10 mM phosphate buffer pH7 for 1 h at RT.

Colony Formation

A PCR template may be hybridised to the grafted primers immediately prior to the PCR reaction. The PCR reaction thus begins with an initial primer extension step rather than template denaturation.

The hybridization procedure begins with a heating step in a stringent buffer (95° C. for 5 minutes in TE) to ensure complete denaturation prior to hybridisation of the PCR template. Hybridization was then carried out in 5×SSC, using template diluted to the desired final concentration. After the hybridization, the chip was washed for 5 minutes with milliQ water to remove salts.

Surface amplification was carried out by thermocycled PCR in an MJ Research thermocycler.

A typical PCR program is as follows:
1—97.5° C. for 0:45
2—X° C. for 1:30
3—73° C. for 1:30
4—Goto 1 [40] times
5—73° C. for 5:00
6—20° C. for 3:00
7—End Since the first step in the amplification reaction was extension of the primers bound to template in the initial hybridisation step the first denaturation and annealing steps of this program are omitted (i.e. the chip is placed on the heating block only when the PCR mix is pumped through the flow cell and the temperature is at 73° C.).

The annealing temperature (X° C., step 2) depends on the primer pair that is used. Experiments have determined an optimal annealing temperature of 57° C. for P5/P7 primers. For other primer-pairs the optimum annealing temperature can be determined by experiment. The number of PCR cycles may be varied if required.

PCR was carried out in a reaction solution comprising 1×PCR reaction buffer (supplied with the enzyme) 1M betain, 1.3% DMSO, 200 μM dNTPs and 0.025 U/μL Taq polymerase.

General features of the solid-phase amplification procedure to produce nucleic acid colonies are as described in International patent applications WO 98/44151 and WO 00/18957.

Linearisation

See procedures described in the specific examples

Thermal Dehybridisation

Thermal denaturation or de-hybridization of linearised colonies was carried out in stringent buffer (TE). Temperature was ramped 0.5° C./sec to 97.5° C. and held at 97.5° C. for 2 minutes 30 seconds.

Hybridisation of Sequencing Primer

The procedure begins with a heating step in a stringent buffer (TE) to ensure complete denaturation of the colonies prior to hybridisation of the primer.

Hybridization was carried out in 5×SSC, using an oligonucleotide diluted to a final concentration of 500 nM. This solution should be prepared just before use, especially when fluorophore-labelled oligonucleotides are used.

Typical temperature cycling profile was as follows:
MJ-Research Thermocycler Program Set:
(Control method: block)
1—0.5° C./sec to 97.5° C.
2—97.5° C. for 2:30
3—97.5° C. for 0:02
  −0.1° C. per cycle
4—Goto 3 for 574 times
5—40° C. for 15:00
6—End

Example 1

Cleavage Evaluation of Diol Primer in 8 Channel (Baccarat) Chip

Oligonucleotides Used:
Labelled P5 Complementary Oligonucleotide (Supplied by Eurogentec):

(SEQ ID NO: 1)
5'-Texas Red-TCGGTGGTCGCCGTATCATT-3'-OH

Grafting Control Primer (Supplied by Eurogentec):

(SEQ ID NO: 2)
5'-phosphorothioate-GTAGACTGCATGACCTGTAG-3'-Cy3

P5 Non-Cleavable Primer (Supplied by Eurogentec):

(SEQ ID NO: 3)
5'-phosphorothioate-TTTTTTTTTTAATGATACGGCGACCACCGA -3'OH

P5 Cleavable Primer (Supplied by Fidelity Systems):

(SEQ ID NO: 4)
5'-phosphorothioate-arm 26-diol22A-AATGATACGGCGACCACCGA-3'OH

The structures of the arm26 and diol22A components were as follows:

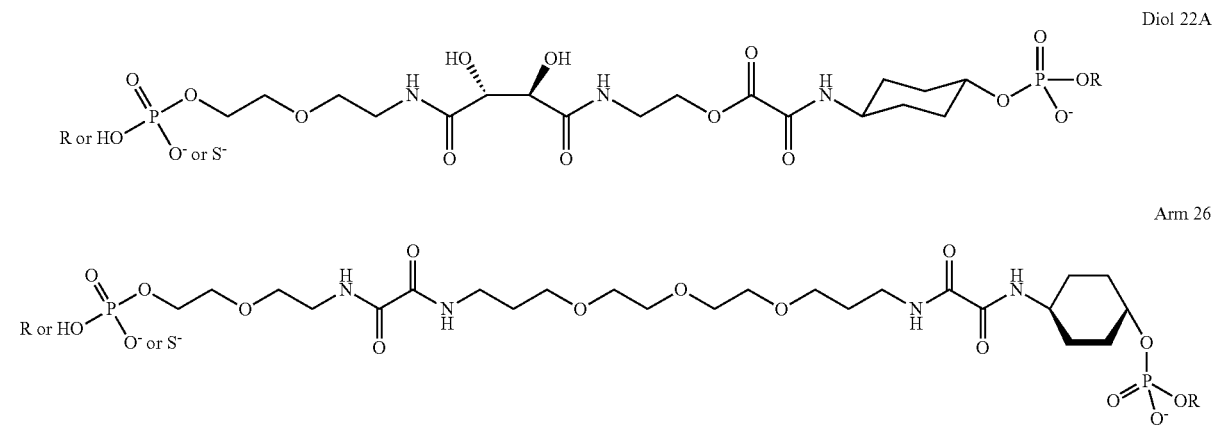

Diol 22A

Arm 26

Grafting was performed according to the procedure described under general methods. Channels 1 and 2 of an 8 channel chip were grafted using the non-cleavable primer, channels 5, 6 and 7 using the cleavable diol linker and channel 8 using the grafting control.

A first hybridization using the complementary P5 oligonucleotide (SEQ ID NO:1) was performed to measure the percentage of P5 oligonucleotides attached to the surface. Standard hybridisation conditions are described in the general methods above. Channels to be cleaved were treated with a solution of 0.1M sodium periodate in water for 30 min at room temperature, channel 1 being kept as a control to evaluate the potential damage of the DNA or the surface by sodium periodate. The channels were then washed for 5 minutes with milliQ water then 5 min 5×SSC buffer at room temperature.

A second hybridization was carried out using the complementary P5 oligonucleotide (SEQ ID NO:1) to evaluate the percentage of non-cleaved oligonucleotide. A second treatment with 0.1M sodium periodate was then performed for 15 min followed by the same washing conditions and a last hybridization using the complementary P5 oligonucleotide. After each hybridization, the chip was scanned using the following settings: focal plane +3 mm, 600V, 610BP/Red (633 nm). The intensities were then normalized.

Results

Figure 4:
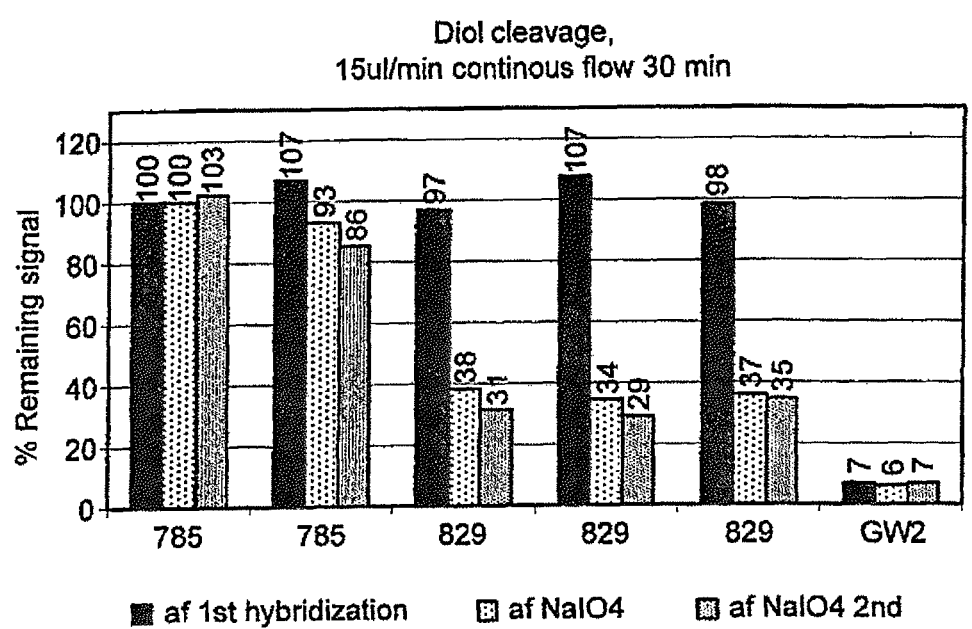
FIG. 4. graphically illustrates cleavage of a diol linker by treatment with sodium periodate.

The results illustrated graphically in FIG. 4 show that the diol linker (SEQ ID NO:4) was cleaved with an efficiency of 70%.

Example 2

Nucleic Acid Colony Formation on Acrylamide (SFA) Coated 8 Channel (Baccarat) Chips Using Diol Primer Oligonucleotides Used:

P5 Non-Cleavable Primer (Supplied by Eurogentec):

(SEQ ID NO: 3)
5'-phosphorothioate-TTTTTTTTTTAATGATACGGCGACCACCGA -3'OH

P7 Non-Cleavable Primer (Supplied by Eurogentec):

(SEQ ID NO: 5)
5'-phosphorothioate- TTTTTTTTTTCAAGCAGAAGACGGCATACGA -3'OH

P5 Cleavable Primer (Supplied by ATD):

5'-phosphorothioate-TTTTTTTTTT-(diol)X3-AATGATACGGCGACCACCGA -3'OH (equivalent to SEQ ID NO:3 but including diol linkage)

The structure of the "diol" linker incorporated into the cleavable primer was as follows:

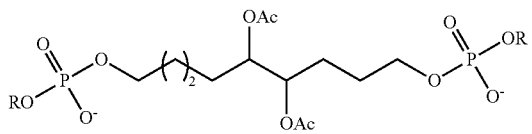

It will be noted that the linker unit is incorporated with the diol in a protected OAc form during oligonucleotide synthesis. The free diol is released by ammonia treatment during oligonucleotide cleavage/deprotection. Therefore, the primers used in the grafting reaction contain the free diol.

Grafting was performed according to the procedure described in the general methods. Channels 1, 2 and 3 of an 8 channel chip were grafted using the non-cleavable pair of P5/P7 primers (SEQ ID NOS 3 and 5), channels 4, 5, 6, 7 and 8 using the cleavable P5 diol primer illustrated above (equivalent to SEQ ID NO:3 but including diol linkage between the polyT portion and the P5 portion) with non-cleavable primer P7 (SEQ ID NO:5).

The template used for amplification was a library of PCR fragments derived from PhiX 174. The fragments contain common "end" sequences enabling amplification with the P5 and P7 primers flanking 400-700 bp fragments of PhiX 174 of unknown sequence. Hybridization of the template was carried out substantially as described in the general methods above using a 100 pM solution of template for channels 2, 3, 4, 5, 6 and 7, channels 1 and 8 being kept as primer only controls. PCR was performed as described in the general methods. Amplification products were then stained with SyBr Green-I in TE buffer (1/10 000), using 100 µl per channel and visualised using objective 0.4, Filter Xf 22 and 1 second acquisition time (gain 1).

Results

Figure 5:
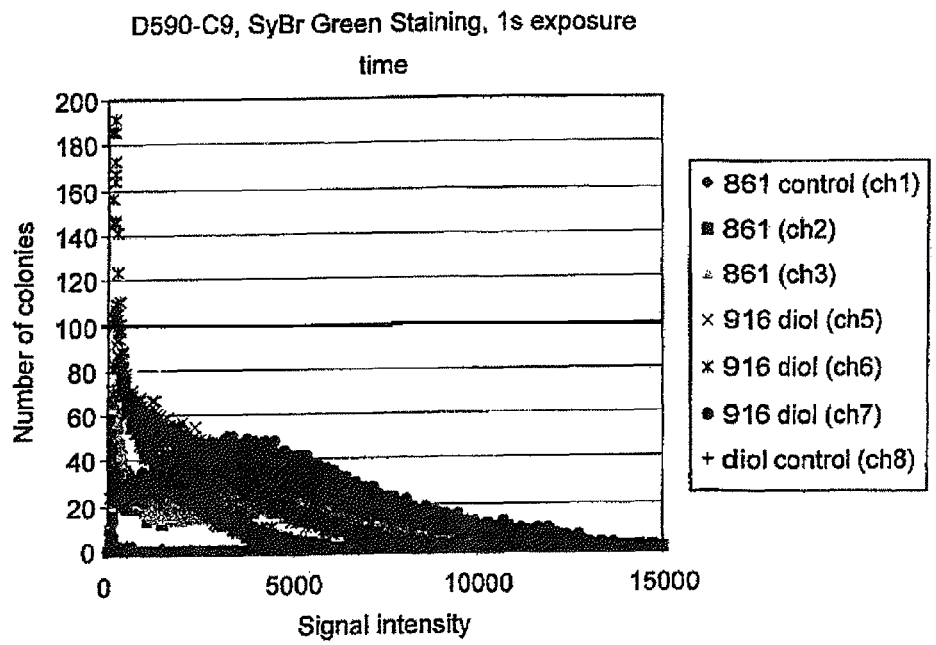
FIG. 5. shows signal intensity versus time for SyBr green stained colonies treated with periodate, illustrating selective cleavage of colonies containing diol linkers.
Figure 6:
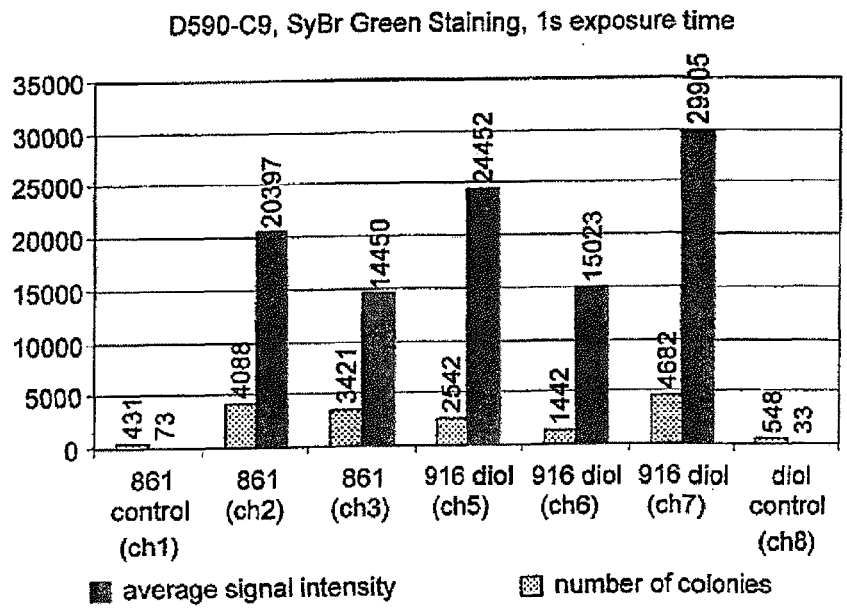
FIG. 6. graphically illustrates cleavage of colonies containing diol linkers.

FIGS. 5 and 6 illustrate that successful colony formation was obtained using the cleavable diol primer.

Example 3

Cleavage and Subsequent Hybridization of Nucleic Acid Colonies Generated on Diol Cleavable Primer Olionucleotide Used:
A594 sequencing primer (supplied by Eurogentec):

```
                                              (SEQ ID NO: 6)
5'-A594- CTGGCACGACAGGTTTCCCGACTGGAAAGCGGGCAGT

G-3'-OH
```

Channels to be cleaved were treated with a solution of 0.1M of sodium periodate and 0.1M ethanolamine in water for 1 hour at room temperature. All the other channels were washed with milliQ water. All channels were then washed for 30 minutes with milliQ water at room temperature.

Hybridization was carried out using the sequencing primer (SEQ ID NO:6) labelled with A594 to evaluate the percentage of non-cleaved oligonucleotide. The sequencing primer was hybridised to the linearised clusters prepared as described above at 500 nM, using standard conditions for hybridisation as described under the general methods. The chip was then imaged using an orange filter with an exposure time of 1 s.

Results

As expected, the channels grafted with the non-cleavable primers (chs 2 and 3) treated or not treated with sodium periodate did not give any hybridization signal with the sequencing primer. As the colonies in these channels are still double-stranded no hybridization of the sequencing primer can occur.

No signal was observed for the cleavable primer treated with milliQ water (no sodium periodate).

Hybridization of the sequencing primer was detected in the two diol channels treated with sodium periodate.

Example 4

Acrylamide Coating of Silex Flowcells

The solid supports used were typically 8-channel glass flowcells such as those provided by Silex Microsystems (Sweden). However, the experimental conditions and procedures are readily applicable to other solid supports.

Figure 7:
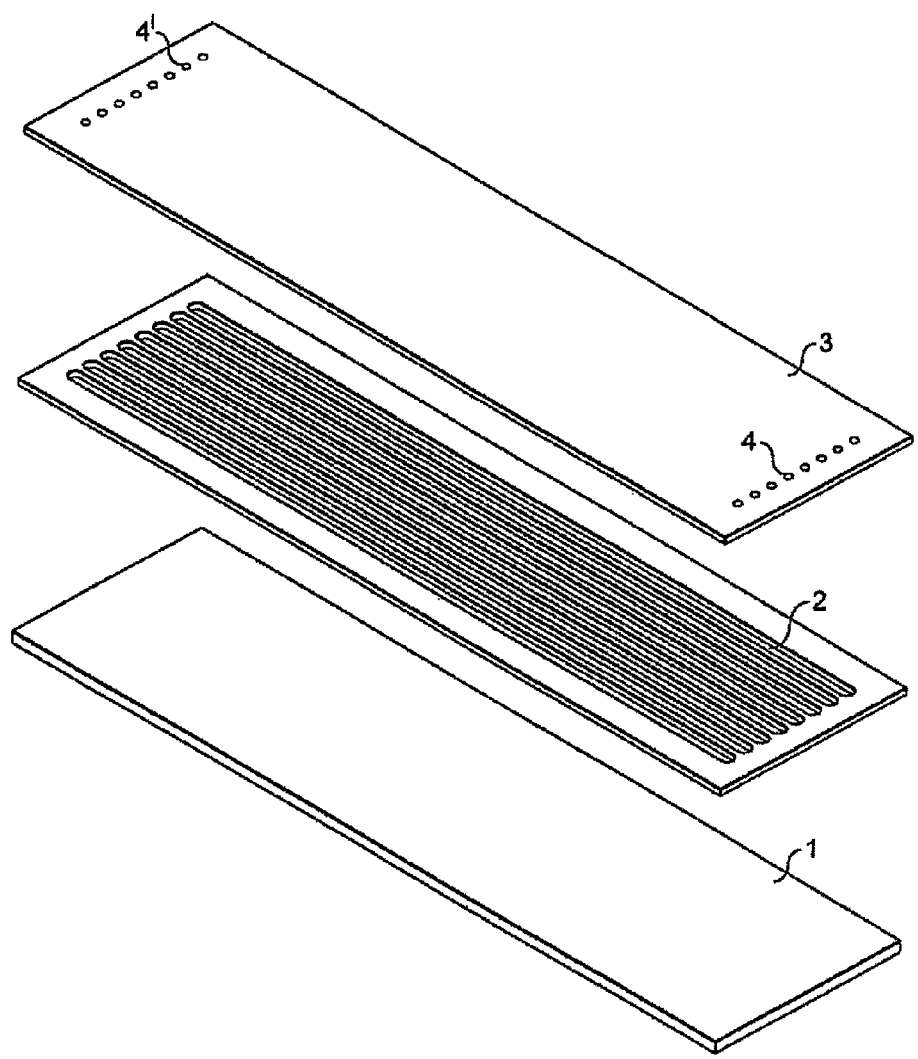
FIG. 7. is a schematic representation of an 8 channel flow-cell suitable for carrying out the methods of the invention.

A schematic representation of one such flowcell is shown in FIG. 7. The flowcell is formed in three layers. The bottom layer 1 is formed of borosilicate glass at a depth of 1000 µm. An etched silicon channel layer (100 µm depth) is placed on top to defined 8 separate reaction channels. Top layer 3 (300 µm depth) includes two separate series of 8 holes 4 and 4' in register with the channels of the etched silicon channel layer in order to provide fluid communication with the contents of the channels when the flowcell is assembled in use.

Flowcells were washed as follows: neat Decon for 30 min, milliQ $H_2O$ for 30 min, NaOH 1N for 15 min, milliQ $H_2O$ for 30 min, HCl 0.1N for 15 min, milliQ $H_2O$ for 30 min.

Polymer Solution Preparation

For 10 ml of 2% polymerisation mix.
10 ml of 2% solution of acrylamide in milliQ $H_2O$
165 µl of a 100 mg/ml N-(5-bromoacetamidylpentyl)acrylamide (BRAPA) solution in DMF (23.5 mg in 235 µl DMF)
11.5 µl of TEMED
100 µl of a 50 mg/ml solution of potassium persulfate in milliQ $H_2O$ (20 mg in 400 µl $H_2O$)

The 10 ml solution of acrylamide was first degassed with argon for 15 min. The solutions of BRAPA, TEMED and potassium persulfate were successively added to the acrylamide solution. The mixture was then quickly vortexed and immediately pumped into the flowcell. Polymerization was then carried out for 1 h 30 at RT. Afterwards the channels were washed with milliQ $H_2O$ for 30 min and filled with 0.1 M potassium phosphate buffer for storage until required.

Example 5

Grafting Primers onto Surface of Acrylamide Coated Silex Flowcell

An acrylamide (SFA) coated flowcell was placed onto a modified MJ-Research thermocycler and attached to a peristaltic pump. Grafting mix consisting of 0.5 µM of a forward primer and 0.5 µM of a reverse primer in 10 mM phosphate buffer (pH 7.0) was pumped into the channels of the flowcell at a flow rate of 60 µl/min for 75 s at 20° C. The thermocycler was then heated up to 51.6° C., and the flowcell incubated at this temperature for 1 hour. During this time, the grafting mix underwent 18 cycles of pumping: grafting mix was pumped in at 15 µl/min for 20 s, then the solution was pumped back and forth (5 s forward at 15 µl/min, then 5 s backward at 15 µl/min) for 180 s. After 18 cycles of pumping, the flowcell was washed by pumping in 5×SSC/5 mM EDTA at 15 μl/min for 300 s at 51.6° C. The thermocycler was then cooled to 20° C.

The primers were typically 5'-phosphorothioate oligonucleotides incorporating any specific sequences or modifications required for cleavage. Their sequences and suppliers varied according to the experiment they were to be used for, and in this case were complementary to the 5'-ends of the template duplex. For the experiment described, the amplified clusters contained a diol linkage in one of the grafted primers. Diol linkages can be introduced by including a suitable linkage into one of the primers used for solid-phase amplification.

The grafted primers contained a sequence of T bases at the 5'-end to act as a spacer group to aid linearisation and hybridization. Synthesis of the diol phosphoramidite is detailed below. Oligonucleotides were prepared using the diol phosphoramidite using standard coupling conditions on a commercial DNA synthesiser. The final cleavage/deprotection step in ammonia cleaves the acetate groups from the protected diol moiety, so that the oligonucleotide in solution contains the diol modification. The sequences of the two primers grafted to the flowcell are:

```
5'-PS-TTTTTTTTTT-Diol-AATGATACGGCGACCACCGA-3'
(equivalent to SEQ ID NO: 3 but including diol
linkage)
And
                                            (SEQ ID NO: 5)
5'-PS-TTTTTTTTTTCAAGCAGAAGACGGCATACGA-3'
```

Example 6

Preparation of Diol-Phosphoramidite for DNA Coupling

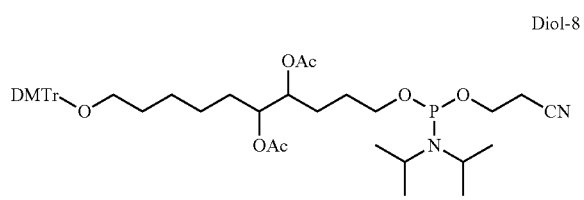

Diol-8

Step 1:

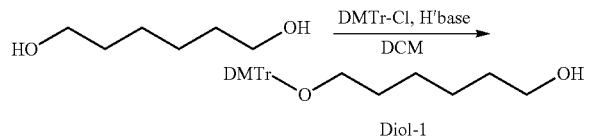

Diol-1

1,6-Hexanediol (Sigma Aldrich 99%) (14.6 g, 124 mmol), N,N-diisopropylethylamine (Hünig's base; Sigma Aldrich; redistilled) (21.6 mL, 124 mmol) was dissolved in anhydrous DCM/DMF (250/50 mL) under $N_2$. The solution was cooled to 0° C. and the first portion of 4,4'-dimethoxytrityl chloride (DMTr-Cl; Sigma-Aldrich 95%) (10.5 g, 31 mmol) added. The reaction mixture was then warmed to room temperature. After stirring for 1 h, the reaction mixture was cooled to 0° C. again and the second portion of DMTr-Cl (10.5 g, 31 mmol) was added and then allowed to stir at room temperature for other 2 hours. TLC (EtOAc: petroleum ether 4:6) analysis indicated ca. 95% consumption of starting material derivative (DMTr-OH). The reaction was concentrated under reduced pressure and Aq. $NaHCO_3$ (sat.) solution (500 mL) was poured into the residue. The resulting mixture was extracted with petroleum ether/EtOAc (2:1) (3×1000 mL). The combined organic layers were dried over $MgSO_4$, and concentrated under vacuum. The residue was co-evaporated with xylene (2×100 mL) to remove DMF. The reaction mixture, was pre-absorbed on silica gel and subjected to flash chromatography using solvents containing 1% $Et_3N$ petroleum ether to petroleum ether/EtOAc (7:3) as eluent. The yield of pale yellow oil was 16.58 g, 64%, with a further 7.8 g (17%) of the bis-tritylated by-product.

TLC: $R_f$: 0.35 (diol-1); $R_f$: 0.7 (bis-tritylated by-product) (petroleum ether/EtOAc 6:4).

$^1$H NMR (400 MHz, $CDCl_3$): δ 1.32-1.44 (m, 4H, 2×$CH_2$), 1.54-1.68 (m, 4H, 2×$CH_2$), 3.06 (t, J=6.6 Hz, 2H, $CH_2O$), 3.62-3.68 (m, 2H, $CH_2OH$), 3.81 (s, 6H, 2×MeO), 6.83-6.85 (m, 4H, Ph), 7.24-7.35 (m, 7H, Ph), 7.45-7.47 (m, 2H, Ph).

Step 2:

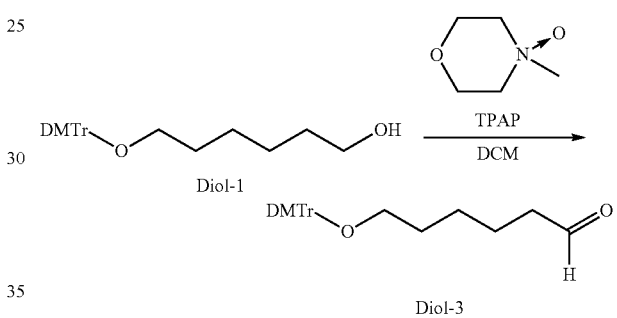

To a solution of Diol-1 (16.6 g, 39.5 mmol) in anhydrous DCM (200 mL), tetrapropylammonium perruthenate (TPAP; Sigma Aldrich 97%) (277 mg, 0.79 mmol) was added under $N_2$ atmosphere. The solution was cooled to 0° C. and N-methylmopholine N-oxide (Sigma Aldrich 97%) (2.7 g, 23 mmol) was added. The reaction was warmed to room temperature. After 1 hour, the other three portions of N-methylmopholine N-oxide (3×2.0 g, 51.2 mmol) were added within a period of four hours. TLC (EtOAc: petroleum ether 4:6) indicated that the reaction goes to completion. The reaction was quenched with aq. $NaHCO_3$ (sat.) (1000 mL) and extracted to $CH_2Cl_2$ (4×1000 mL). The combined organic layers were dried over $MgSO_4$. The solution was concentrated under reduced pressure. Diol-3, 9.9 g, 60%, was isolated by flash chromatography using solvents containing 1% $Et_3N$ from petroleum ether to petroleum ether/EtOAc (6:4) as eluent, as a pale yellow oil.

TLC: $R_f$: 0.7 (petroleum ether/EtOAc 6:4).

$^1$H NMR (400 MHz, $CDCl_3$): δ 1.30-1.37 (m, 2H, $CH_2$), 1.48-1.57 (m, 4H, 2×$CH_2$), 2.34 (td, J=1.7 and 7.4 Hz, 2H, $CH_2CHO$), 2.97 (s, 2H, $CH_2O$), 3.72 (s, 6H, 2×MeO), 6.73-6.76 (m, 4H, Ph), 7.10-7.26 (m, 7H, Ph), 7.34-7.36 (m, 2H, Ph), 9.67 (t, J=1.7, 1H, CHO).

Step 3:

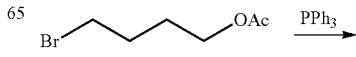

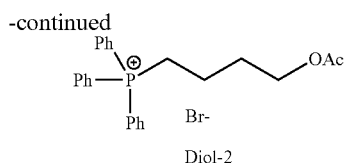

Diol-2

A solution of triphenylphosphine (Sigma-Aldrich 99%, ReagentPlus™). (39.3 g, 150 mmol) and 4-bromobutyl acetate (Sigma-Aldrich) (26 mL, 180 mmol) in anhydrous toluene (300 mL) was heated under reflux for 36 hours under $N_2$ in an oil-bath (140° C.). During the reflux, oil was precipitated out. The reaction mixture was cooled to room temperature. TLC (petroleum ether/EtOAc 7:3) analysis of the toluene solution showed that there was still triphenylphosphine ($R_f$: 0.8) left. The supernatant was decanted into another round-bottomed flask and concentrated down to the approximate volume of 30 mL. The solution was heated under reflux again for another 12 hours. The supernatant was decanted. The portions of oil were combined together, dissolved in water (500 mL) and extracted with EtOAc (2×500 mL). The combined organic layers were back-extracted with water (150 mL). Two lots of aqueous layers were combined, evaporated under reduced pressure. The resulting residue was co-evaporated with acetonitrile (2×100 mL) to give 78.4 g, 95% yield of a pale yellow oil. NMR indicates that the product was pure, and was used for the next step reaction without further purification.

TLC: $R_f$: 0.0 (petroleum ether/EtOAc 7:3).

$^1$H NMR (400 MHz, $CDCl_3$): δ 1.63-1.73 (m, 2H, $CH_2$), 1.94 (s, 3H, 2×$CH_3$), 2.06-2.16 (m, 2H, $CH_2$), 3.97-4.05 (m, 2H, $CH_2P$), 4.11 (t, J=6.0, 2H, $CH_2O$), 7.69-7.95 (m, 15H, Ph).

$^{31}$P NMR (162 MHz, $CDCl_3$): 25.9 ppm.

Mass spec details: LC-MS (Electrospray positive): ($M^+$) 377.

Step 4:

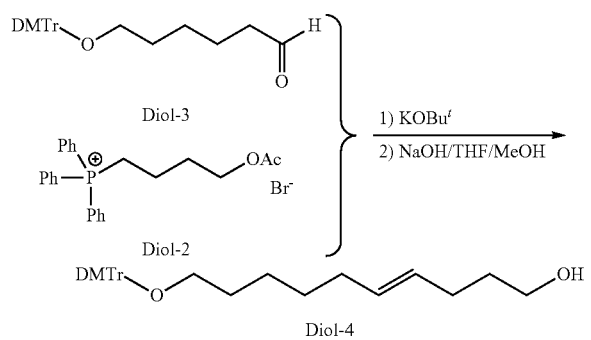

Diol-2 (10.34 g, 22.7 mmol) was weighed into a round-bottomed flask and dissolved with DCM (20 mL). The solution was then evaporated under reduced pressure until it gave a white foam. The flask was then subjected to high vacuum for 24 h. To this flask, anhydrous THF (180 mL) was added under $N_2$. The resulting suspension was cooled to −78° C. with an acetone-dry ice bath. With vigorous stirring, KOBu$^t$ (3.3 g, 29.5 mmol) was added under $N_2$. Slowly the colour of the suspension turned orange, and white solids were gradually precipitated out. To this suspension, a solution of diol-3 (dried at 60° C. under high vacuum for 1 h before the reaction), (9.5 g, 22.7 mmol) in THF (50 mL) was added drop wise over half an hour. The acetone-dry ice bath was then removed. The reaction mixture was slowly warmed up to room temperature and stirred for another hour. The colour of the reaction mixture turned into yellow after the addition of diol-3. The reaction mixture was concentrated down under reduced pressure. The resulting residue was partitioned between DCM (800 mL) and aq. NaCl (sat.) (800 mL). The aqueous layer was extracted with an additional DCM (2×800 mL). The organic extractions were combined, dried over $MgSO_4$, filtered, and evaporated under reduced pressure to give yellow oil. The oil was dissolved in THF/MeOH (125/100 mL) and cooled to 0° C. To this solution, NaOH (1M in $H_2O$, 25 mL) was added. After allowing the reaction to stir for 1 hour, TLC analysis indicated full consumption of starting material. The reaction mixture was neutralized with acetic acid (1.5 mL). The reaction mixture was concentrated down under reduced pressure. The resulting residue was partitioned between DCM (800 mL) and aq. $NaHCO_3$ (sat.) (800 mL). The aqueous layer was extracted with additional DCM (2×800 mL). The organic extractions were combined, dried over $MgSO_4$, filtered, and evaporated to give a pale yellow oil. Diol-4, 6.45 g, 60% was isolated by flash chromatography using solvents containing 1% $Et_3N$ from petroleum ether to petroleum ether/EtOAc (5:5) as eluent, as a light yellow oil.

TLC: $R_f$=0.45 (petroleum ether/EtOAc 6:4).

$^1$H NMR (400 MHz, $CDCl_3$) δ 1.24-1.32 (m, 4H, 2×$CH_2$), 1.54-1.57 (m, 4H, 2×$CH_2$), 1.93-1.96 (m, 2H, $CH_2$), 2.02-2.07 (m, 2H, $CH_2$), 2.96 (t, J=6.6 Hz, 2H, $CH_2O$), 3.54-3.59 (m, 2H, $CH_2OH$), 3.72 (s, 6H, 2×MeO), 5.29-5.32 (m, 2H, 2×=CH), 6.73-6.77 (m, 4H, Ph), 7.11-7.27 (m, 7H, Ph), 7.36-7.38 (m, 2H, Ph).

Step 5:

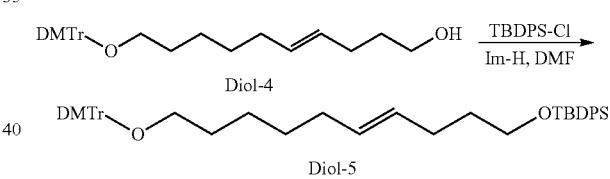

To a solution of Diol-4 (5.68 g, 12 mmol) and imidazole (Sigma Aldrich, 99%), (1.63 g, 24 mmol) in anhydrous DMF (100 mL), t-butyldiphenylsilyl chloride (Sigma Aldrich, 98%), (4.05 mL, 15.6 mmol) was added drop wise under $N_2$ atmosphere at room temperature. The reaction was stirred for 1 hour. TLC (petroleum ether/EtOAc 8:2) indicated that the starting material was fully consumed. A saturated aq. $NaHCO_3$ solution (500 mL) was added to quench the reaction. The resulting mixture was extracted with petroleum ether/EtOAc (2:1) (3×500 mL). The organic layers were combined, dried over $MgSO_4$, filtered, and evaporated to give a yellow oil. Diol-5, 8.14 g, 95% was isolated by flash chromatography using solvents containing 1% $Et_3N$ from petroleum ether to petroleum ether/EtOAc (9:1) as eluent, as a colourless oil.

TLC: $R_f$=0.7 (petroleum ether:EtOAc 8:2).

$^1$H NMR (400 MHz, $CDCl_3$): δ 0.97 (s, 9H, 3×Me), 1.19-1.30 (m, 4H, 2×$CH_2$), 1.48-1.55 (m, 4H, 2×$CH_2$), 1.91-1.95 (m, 2H, $CH_2$), 2.01-2.06 (m, 2H, $CH_2$), 2.95 (t, J=6.6 Hz, 2H, $CH_2O$), 3.58 (t, J=6.3 Hz, 2H, $CH_2O$), 3.70 (s, 6H, 2×MeO), 5.24-5.27 (m, 2H, 2×=CH), 6.72-6.75 (m, 4H, Ph), 7.11-7.37 (m, 15H, Ph), 7.57-7.60 (m, 4H, Ph).

Step 6:

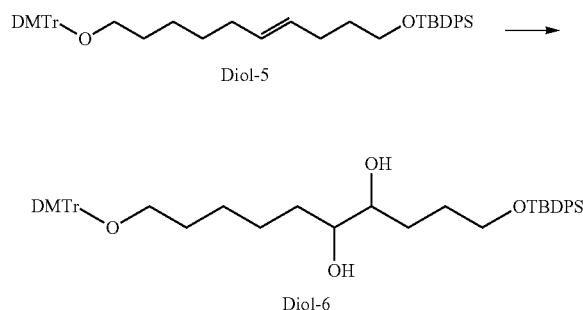

A mixture of diol-5 (9.27 g, 13 mmol), AD-mix-α (Sigma Aldrich), (18.2 g), methanesulfonamide (Sigma Aldrich, 97%), (1.23 g, 13 mmol), t-BuOH (65 mL) and water (65 mL) was stirred together vigorously at 55° C. for 14 h. The TLC analysis (petroleum ether:EtOAc 6:4) indicated ca. 95% consumption of the starting material. The reaction mixture was cooled to room temperature, treated with sodium sulfite (15.3 g, 12 mmol), then further stirred for 30 min. A saturated aq. NaHCO$_3$ solution (500 mL) was added to the reaction. The resulting mixture was extracted with EtOAc (3×500 mL). The organic layers were combined, dried over MgSO$_4$, filtered, and evaporated to give yellow oil. Diol-6, 7.96 g, 82%, was isolated by flash chromatography (silica gel, Fluka, 70-230 mesh) using solvents containing 1% Et$_3$N from petroleum ether to petroleum ether/EtOAc (1:1) as elutant, as a white solid.

TLC: R$_f$=0.3 (petroleum ether:EtOAc 6:4).

$^1$H NMR (400 MHz, CDCl$_3$) δ 1.07 (s, 9H, 3×Me), 1.41-1.7 (m, 12H, 6×CH$_2$), 1.94 (d, J=4.3 Hz, 1H, OH), 2.94-2.95 (m, 1H, OH), 3.06 (t, J=6.6 Hz, 2H, CH$_2$O), 3.61-3.63 (m, 2H, 2×CHOH), 3.73 (t, J=5.6 Hz, 2H, CH$_2$O), 3.81 (s, 6H, 2×MeO), 5.24-5.27 (m, 2H, 2×=CH), 6.82-6.85 (m, 4H, Ph), 7.21-7.47 (m, 15H, Ph), 7.57-7.60 (m, 4H, Ph).

Step 7:

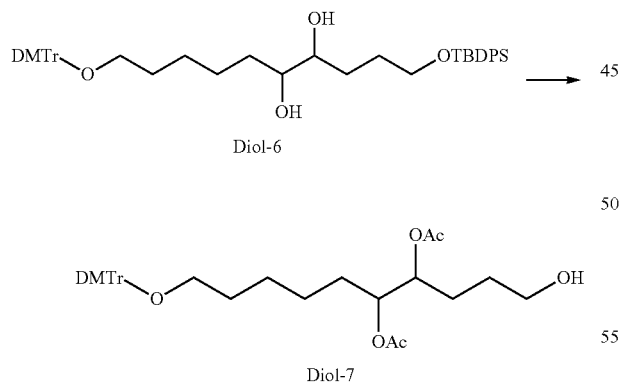

To a solution of diol-6 (7.96 g, 13 mmol) and DMAP (Sigma-Aldrich ReagentPlus™, 99%). (260 mg, 2.13 mmol) in a mixture of pyridine (15 mL) and DCM (30 mL), acetic anhydride (Fluka 99%), (2.5 mL, 26.68 mmol) was added at room temperature. TLC analysis (petroleum ether:EtOAc 6:4) indicated full consumption of the starting material after 1 h. The reaction was quenched by saturated aq. NaHCO$_3$ solution (500 mL). After 5 min. the mixture was extracted with DCM (3×500 mL). The organic layers were combined, dried over MgSO$_4$, filtered, and evaporated. The residue was co-evaporated with toluene (2×100 mL). The resulting yellow oil was subjected to a plug of silica gel (50 g, Fluka, 70-230 mesh) to remove DMAP using eluents containing 0.1% Et$_3$N from petroleum ether to petroleum ether/EtOAc (7:3) (250 mL each). The combined fractions of product were concentrated to dryness. The resulting colourless oil was dissolved in THF (100 mL) and treated with TBAF (Sigma-Aldrich; 5% wt water), (1 M in THF, 15 mL) at 0° C. The reaction solution was slowly warmed up to room temperature and stirred for further 2 hours. TLC analysis (petroleum ether:EtOAc 6:4) indicated that desilylation was completed. The volatile solvent (THF) was evaporated under reduced pressure at low temperature. A saturated aq. NaHCO$_3$ solution (500 mL) was added to the residue. The resulting mixture was extracted with EtOAc (3×500 mL). The organic layers were combined, dried over MgSO$_4$, filtered, and evaporated to give yellow oil. Diol-7, 4.2 g, 66%, was isolated by flash chromatography using solvents containing 1% Et$_3$N from petroleum ether to petroleum ether/EtOAc (1:1) as elutant, as a white solid.

TLC: R$_f$=0.45 (petroleum ether:EtOAc 1:1).

$^1$H NMR (400 MHz, CDCl$_3$) δ 1.29-1.33 (m, 4H, 2×CH$_2$), 1.47-1.63 (m, 8H, 4×CH$_2$), 1.99, 2.01 (2s, 6H, 2 MeC(O)), 3.00 (t, J=6.5 Hz, 2H, CH$_2$O), 3.60-3.64 (m, 2H, CH$_2$O), 3.75 (s, 6H, 2×MeO), 4.92-4.97 (m, 2H, 2×CHOAc), 6.76-6.80 (m, 4H, Ph), 7.15-7.29 (m, 7H, Ph), 7.38-7.40 (m, 2H, Ph).

Step 8:

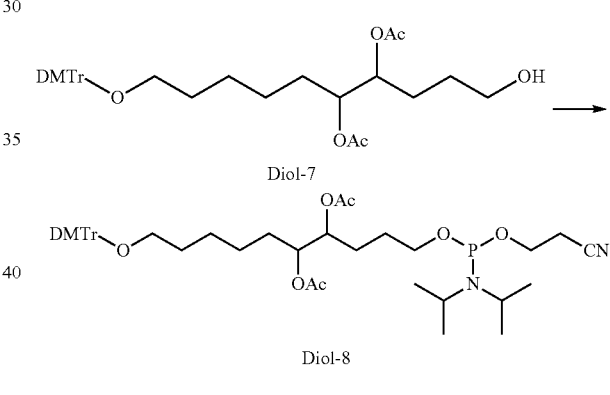

To a solution of diol-7 (2.08 g, 3.5 mmol) and diisopropylethylamine (Sigma Aldrich), (1.53 ml, 8.75 mmol) in DCM (17 mL), 2-cyanoethyl N,N-diisopropylchlorophosphoramidite (1.0 g, 4.2 mmol) was added drop wise at room temperature under N$_2$. After stirring for 1 hour, TLC analysis (petroleum ether:EtOAc 4:6) indicated full consumption of the starting material. The solvent (THF) was concentrated under reduced pressure. The resulting residue was subjected to chromatography directly. Diol-8, 2.5 g, 90%, was isolated by flash chromatography using solvents containing 1% Et$_3$N from petroleum ether to petroleum ether/EtOAc (1:1) as eluent, as a colourless syrup.

TLC: R$_f$=0.55 (petroleum ether:EtOAc 4:6).

$^1$H NMR (400 MHz, CDCl$_3$) δ 1.09, 1.10, 1.11, 1.12 (4 s, 12H, N(CHMe$_2$)$_2$), 1.26-1.31 (m, 4H, 2×CH$_2$), 1.45-1.56 (m, 8H, 4×CH$_2$), 1.95, 1.969, 1.971, 1.98 (4 s, 6H, 2 MeCO), 2.56 (t, J=6.5 Hz, 2H, CH$_2$CN), 2.95 (t, J=6.5 Hz, 2H, CH$_2$O), 3.49-3.55 (m, 4H, CH$_2$O), 3.72 (s, 6H, 2×MeO), 4.89-4.92 (m, 2H, 2×CHOAc), 6.74-6.76 (m, 4H, Ph), 7.13-7.25 (m, 7H, Ph), 7.34-7.37 (m, 2H, Ph).

$^{31}$P NMR (162 MHz, CDCl$_3$): 148.67, 148.69 ppm.

Example 7

Formation of DNA Colonies (Clusters) on Silex Chips

Step 1: Hybridisation and Amplification

Figure 8:
FIG. 8. illustrates the structure and sequence of an exemplary DNA template (top strand, SEQ ID NO:8; bottom strand, SEQ ID NO:11) used for solid-phase PCR amplification in the accompanying examples. Sequences of the amplification primers P5 and P7 are shown in bold type. The sequencing primer for the insert is also shown (SEQ ID NO:7).

The DNA sequence used in the amplification process was a single monotemplate sequence of 364 bases, with ends complimentary to the grafted primers. The full sequence of the template duplex is shown in FIG. 8 (SEQ ID NO:8). The duplex DNA (1 nM) was denatured using 0.1 M sodium hydroxide treatment followed by snap dilution to the desired 0.2-2 µM 'working concentration' in 'hybridization buffer' (5×SSC/0.1% tween).

Surface amplification was carried out by thermocycling using an MJ Research thermocycler, coupled with an 8-way peristaltic pump Ismatec IPC ISM931 equipped with Ismatec tubing (orange/yellow, 0.51 mm ID).

The single stranded template was hybridised to the grafted primers immediately prior to the amplification reaction, which thus begins with an initial primer extension step rather than template denaturation. The hybridization procedure begins with a heating step in a stringent buffer to ensure complete denaturation prior to hybridisation.

After the hybridization, which occurs during a 20 min slow cooling step, the flowcell was washed for 5 minutes with a wash buffer (0.3×SSC/0.1% tween).

A typical amplification process is detailed in the following table, detailing the flow volumes per channel:

| Step | Description | T (° C.) | Time (sec) | Flow rate (µl/min) | Pumped V (µl) |
|---|---|---|---|---|---|
| 1 | Pump Hybridization pre-mix | 20 | 120 | 60 | 120 |
| 2 | Pump Hybridization mix | 98.5 | 300 | 15 | 75 |
| 3 | Remove bubbles | 98.5 | 10 | 100 | 16.7 |
| 4 | Stop flow and hold T | 98.5 | 30 | static | 0 |
| 5 | Slow cooling | 98.5-40.2 | 19.5 min | static | 0 |
| 6 | Pump wash buffer | 40.2 | 300 | 15 | 75 |
| 7 | Pump amplification pre-mix | 40.2 | 200 | 15 | 50 |
| 8 | Pump amplification mix | 40.2 | 75 | 60 | 75 |
| 9 | First Extension | 74 | 90 | static | 0 |
| 10 amp cycles 1 to 30 | Denaturation | 98.5 | 45 | static | 0 |
| | Re-fill channels | 98.5 | 10 | 60 | 10 |
| | Annealing | 58 | 90 | static | 0 |
| | Extension | 74 | 90 | static | 0 |
| 11 | Hold at 20° C. | 20 | for ever | static | 0 |
| 12 | Pump wash buffer | 74 | 300 | 15 | 75 |

Hybridisation pre mix (buffer)=5×SSC/0.1% tween
Hybridisation mix=0.1 M hydroxide DNA sample, diluted in hybridisation pre mix
Wash buffer=0.3×SSC/0.1% tween
Amplification pre mix=2 M betaine, 20 mM Tris, 10 mM Ammonium Sulfate, 2 mM Magnesium sulfate, 0.1% Triton, 1.3% DMSO, pH 8.8
Amplification mix=2 M betaine, 20 mM Tris, 10 mM Ammonium Sulfate, 2 mM Magnesium sulfate, 0.1% Triton, 1.3% DMSO, pH 8.8 plus 200 µM dNTP mix and 25 units/mL of Taq polymerase (NEB Product ref M0273L)

Step 2: Linearisation

To linearize the nucleic acid clusters formed within the flow cell channels, the computer component of the instrumentation flowed the appropriate linearization buffer through the flow cell for 20 mins at room temp at 15 µL/min (total volume=300 µL per channel), followed by water for 5 mins at r.t.

The linearisation buffer consisted of 1429 µL of water, 64 mg of sodium periodate, 1500 µL of formamide, 60 µL of 1 M Tris pH 8, and 11.4 µL of 3-aminopropanol, mixed for a final volume of 3 mL. The periodate was first mixed with the water while the Tris was mixed with the formamide. The two solutions were then mixed together and the 3-aminopropanol added to that mixture.

Step 3: Blocking Extendable 3'-OH Groups

To prepare the blocking pre-mix, 1360 µL of water, 170 µL of 10× blocking buffer (NEB buffer 4; product number B7004S), and, 170 µL of cobalt chloride (25 mM) were mixed for a final volume of 1700 µL. To prepare the blocking mix 1065.13 µL of blocking pre-mix, 21.12 µL of 125 µM ddNTP mix, and 13.75 µL of TdT terminal transferase (NEB; part no M0252S) were mixed for a final volume of 1100 µL.

To block the nucleic acid within the clusters formed in the flow cell channels, the computer component of the instrumentation flowed the appropriate blocking buffer through the flow cell, and controlled the temperature as shown in the exemplary embodiments below.

| Step | Description | T (° C.) | Time (sec) | Flow rate (µl/min) | Pumped V (µl) |
|---|---|---|---|---|---|
| 1 | Pump Blocking pre-mix | 20 | 200 | 15 | 50 |
| 2 | Pump Blocking mix | 37.7 | 300 | 15 | 75 |
| 3 | Stop flow and hold T | 37.7 | 20 | static | 0 |

-continued

| Step | Description | T (° C.) | Time (sec) | Flow rate (µl/min) | Pumped V (µl) |
|---|---|---|---|---|---|
| 4 | Cyclic pump Blocking mix and wait | 37.7 | 8 × (20 + 180) | 15/static | 45 |
| 5 | Pump wash buffer | 20 | 300 | 15 | 75 |

Step 4: Denaturation and Hybridization of Sequencing Primer

To prepare the primer mix, 895.5 µL of hybridization pre-mix/buffer and 4.5 µl of sequencing primer (100 µM) were mixed to a final volume of 900 µL. The sequence of the sequencing primer used in this reaction was:

(SEQ ID NO: 7)
5'-ACACTCTTTCCCTACACGACGCTCTTCCGATC-3'

To denature the nucleic acid within the clusters and to hybridize the sequencing primer, the computer component of the instrumentation flowed the appropriate solutions through the flow cell as described below:

| Step | Description | T (° C.) | Time (sec) | Flow rate (μl/min) | Pumped V (μl) |
|---|---|---|---|---|---|
| 1 | Pump NaOH | 20 | 300 | 15 | 75 |
| 2 | Pump TE | 20 | 300 | 15 | 75 |
| 3 | Pump Primer mix | 20 | 300 | 15 | 75 |
| 4 | Hold at 60 C | 60 | 900 | 0 | 0 |
| 5 | Pump wash buffer | 40.2 | 300 | 15 | 75 |

After denaturation and hybridization of the sequencing primer, the flowcell was ready for sequencing.

Example 8

DNA Sequencing Cycles

Sequencing was carried out using modified nucleotides prepared as described in International patent application WO 2004/018493, and labelled with four different commercially available fluorophores (Molecular Probes Inc.).

A mutant 9° N polymerase enzyme (an exo-variant including the triple mutation L408Y/Y409A/P410V and C223S) was used for the nucleotide incorporation steps.

Incorporation mix, Incorporation buffer (50 mM Tris-HCl pH 8.0, 6 mM MgSO4, 1 mM EDTA, 0.05% (v/v) Tween –20, 50 mM NaCl) plus 110 nM YAV exo- C223S, and 1 μM each of the four labelled modified nucleotides, was applied to the clustered templates, and heated to 45° C.

Templates were maintained at 45° C. for 30 min, cooled to 20° C. and washed with Incorporation buffer, then with 5×SSC/0.05% Tween 20. Templates were then exposed to Imaging buffer (100 mM Tris pH 7.0, 30 mM NaCl, 0.05% Tween 20, 50 mM sodium ascorbate, freshly dissolved).

Templates were scanned in 4 colours at room temp.

Templates were then exposed to sequencing cycles of Cleavage and Incorporation as follows:

Cleavage
  Prime with Cleavage buffer (0.1 M Tris pH 7.4, 0.1 M NaCl and 0.05% Tween 20). Heat to 60° C.
  Treat the clusters with Cleavage mix (100 mM TCEP in Cleavage buffer).
  Wait for a total of 15 min in addition to pumping fresh buffer every 4 min.
  Cool to 20° C.
  Wash with Enzymology buffer.
  Wash with 5×SSC/0.05% Tween 20.
  Prime with Imaging buffer.
  Scan in 4 colours at RT.
Incorporation
  Prime with Incorporation buffer Heat to 60° C.
  Treat with Incorporation mix. Wait for a total of 15 min in addition to pumping fresh Incorporation mix every 4 min.
  Cool to 20° C.
  Wash with Incorporation buffer.
  Wash with 5×SSC/0.05% Tween 20.
  Prime with imaging buffer.
  Scan in 4 colours at RT.
  Repeat the process of Incorporation and Cleavage for as many cycles as required.

Figure 9:
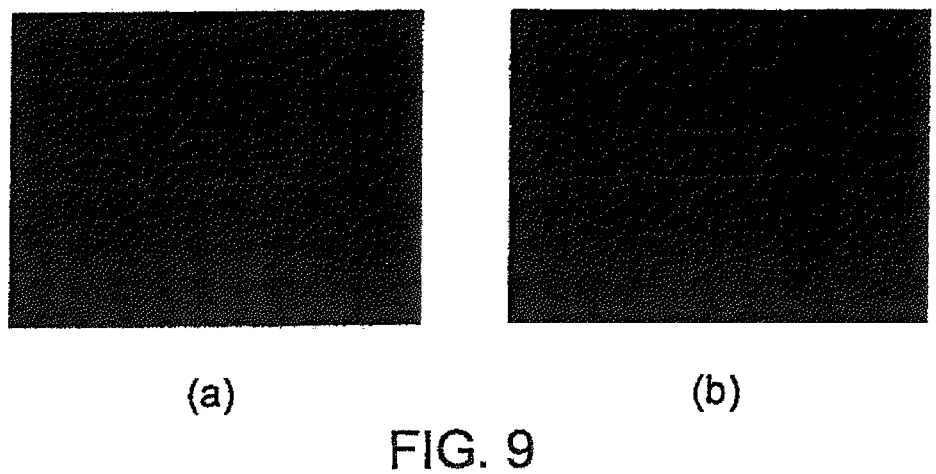
FIG. 9. shows fluorescent CCD images of clustered arrays of nucleic acid colonies following a single cycle of nucleotide incorporation under standard sequencing conditions. Panel (A) illustrates nucleotide incorporation on colonies of nucleic acids which have not been linearised. Pnale (B) illustrates nucleotide incorporation of colonies of nucleic acid templates which have been linearised by periodate cleavage of a diol linker.
Figure 10:
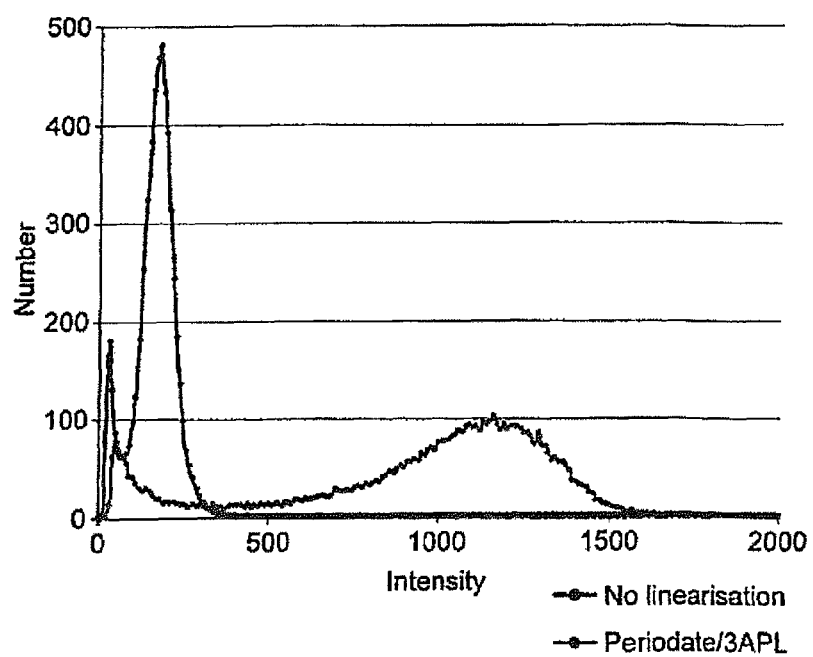
FIG. 10. shows histogram plots (fluorescence intensity vs number of colonies) corresponding to the fluorescent CCD images shown in FIG. 9.

Incorporated nucleotides were detected using a total internal reflection based fluorescent CCD imaging apparatus. Images were recorded and analysed to measure the intensities and numbers of the fluorescent objects on the surface. Images of two tiles from the first cycle of nucleotide incorporation for a linearised and a non-linearised (no periodate) channel are shown in FIG. 9. The histogram plots of these tiles are shown in FIG. 10. In the case of the sequence selected for amplification, only a single base (T) was incorporated in each cluster. This figure clearly shows the presence of clusters in both the linearised and non linearised channels, but the linearised clusters show a far higher average signal intensity. In the absence of the linearisation step, the clusters remain double stranded, and can not undergo effective hybridisation with a sequencing primer, and therefore show greatly reduced signal upon treatment with nucleotides and polymerase.

The invention claimed is:

1. A method of generating a template for a nucleic acid sequencing reaction comprising, (i) providing a solid support comprising a plurality of forward amplification primers and a plurality of reverse amplification primers, wherein said plurality of forward amplification primers or said plurality of reverse amplification primers comprises one or more methylated nucleotides;

(ii) amplifying a template using the primers on the support to produce a plurality of double-stranded nucleic acid molecules, wherein both strands of the molecules are attached to the solid support at their 5' ends, thereby producing a hemimethylated duplex structure in each double-stranded nucleic acid molecule;

(iii) cleaving one strand of the double stranded molecules at said hemimethylated duplex structure with an endonuclease enzyme specific for a recognition sequence including the one or more methylated nucleotides;

(iv) subjecting the cleaved strand to denaturing conditions to remove the portion of the cleaved strand not attached to the solid support, thereby generating partially or substantially single-stranded templates for a nucleic acid sequencing reaction.

2. The method of claim 1, wherein the double-stranded nucleic acid molecules each comprise a target region flanked by non-target sequences derived from the amplification primers used for amplification.

3. The method of claim 2, wherein the recognition sequence including the one or more methylated nucleotides is located within the non-target sequences of the double-stranded nucleic acid molecules.

4. The method of claim 1, wherein amplification of the template forms a cluster comprising the plurality of double-stranded molecules.

5. The method of claim 1, further comprising performing a sequencing reaction to determine the sequence of at least one region of the partially or substantially single-stranded templates.

6. The method of claim 5, wherein the sequence of said at least one region of the partially or substantially single-stranded templates is determined.

7. The method of claim 5, wherein the sequencing reaction comprises sequencing-by-synthesis.

8. The method of claim 5, wherein the sequencing reaction comprises pyrosequencing or sequencing-by-ligation.

9. The method of claim 1, wherein the solid support comprises a hydrogel.

10. The method of claim 9, wherein the hydrogel is a polyacrylamide hydrogel.

11. The method of claim 9, wherein the solid support is prepared by a method comprising polymerizing on the solid support a mixture of:

(i) a first comonomer which is acrylamide, methacrylamide, hydroxyethyl methacrylate or N-vinyl pyrrolidinone; and (ii) a second comonomer which is a functionalized acrylamide or acrylate of formula (I):

$$H_2C=C(H)-C(=O)-A-B-C \quad (I);$$

or a methacrylate or methacrylamide of formula (II):

$$H_2C=C(CH_3)-C(=O)-A-B-C \quad (II);$$

wherein

A is NR or O, wherein R is hydrogen or an optionally substituted saturated hydrocarbyl group comprising 1 to 5 carbon atoms;

B is an optionally substituted alkylene biradical of formula —(CHn)- wherein n is an integer from 1 to 50; and wherein n=2 or more, one or more optionally substituted ethylene biradicals —CH2CH2- of said alkylene biradical may be independently replaced by ethenylene and ethynylene moieties; and wherein n=1 or more, one or more methylene biradicals —CH2- may be replaced independently with an optionally substituted mono- or polycyclic hydrocarbon biradical comprising from 4 to 50 carbon atoms, or a corresponding deteromonocyclic or heteropolycyclic biradical wherein at least 1 CH2 or CH2 is substituted by an oxygen sulfur or nitrogen atom or an NH group; and C of A-B—C of formulas (I) or (II) is a group for reaction with a compound to bind said compound covalently to said hydrogel to form a polymerized product, characterized in that polymerization is conducted on and immobilized the polymerized product to a solid support that is not covalently surface-modified.

* * * * *

UNITED STATES PATENT AND TRADEMARK OFFICE
CERTIFICATE OF CORRECTION

PATENT NO. : 8,715,966 B2  Page 1 of 1
APPLICATION NO. : 13/450920
DATED : May 6, 2014
INVENTOR(S) : Xiaohai Liu et al.

It is certified that error appears in the above-identified patent and that said Letters Patent is hereby corrected as shown below:

In the Claims

In Claim 11, at Column 46, Line 21: delete "deteromonocyclic" and insert -- heteromonocyclic --, therefor.

Signed and Sealed this
Twenty-third Day of September, 2014

Michelle K. Lee
*Deputy Director of the United States Patent and Trademark Office*